US012234332B2

United States Patent
Nakatomi et al.

(10) Patent No.: US 12,234,332 B2
(45) Date of Patent: Feb. 25, 2025

(54) NUCLEATING AGENT FOR POLYOLEFIN RESIN, NUCLEATING AGENT COMPOSITION FOR POLYOLEFIN RESIN CONTAINING SAME, MASTER BATCH FOR POLYOLEFIN RESIN, POLYOLEFIN RESIN COMPOSITION, MOLDED ARTICLE THEREOF, FILM THEREOF, METHOD FOR PRODUCING POROUS FILM, AND PACKAGE

(71) Applicant: ADEKA CORPORATION, Tokyo (JP)

(72) Inventors: Minako Nakatomi, Saitama (JP); Naoto Ueda, Saitama (JP); Shogo Masai, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 964 days.

(21) Appl. No.: 17/279,034

(22) PCT Filed: Nov. 6, 2019

(86) PCT No.: PCT/JP2019/043540
§ 371 (c)(1),
(2) Date: Mar. 23, 2021

(87) PCT Pub. No.: WO2020/137179
PCT Pub. Date: Jul. 2, 2020

(65) Prior Publication Data
US 2021/0403655 A1 Dec. 30, 2021

(30) Foreign Application Priority Data

Dec. 27, 2018 (JP) .................................. 2018-246275
Apr. 2, 2019 (JP) .................................. 2019-070797
Jul. 17, 2019 (JP) .................................. 2019-132216

(51) Int. Cl.
*C08J 5/18* (2006.01)
*B29B 11/06* (2006.01)
(Continued)

(52) U.S. Cl.
CPC ................. *C08J 5/18* (2013.01); *B29B 11/06* (2013.01); *B29C 55/005* (2013.01); *B29C 55/02* (2013.01);
(Continued)

(58) Field of Classification Search
CPC ....... C07C 233/63; C07C 233/83; C08K 5/20; C08L 2205/24
See application file for complete search history.

(56) References Cited

U.S. PATENT DOCUMENTS 5,998,576 A 12/1999 Sadamitsu et al.
6,235,823 B1 5/2001 Ikeda et al.
(Continued)

FOREIGN PATENT DOCUMENTS

CN 102510877 A 6/2012
CN 102976969 A 3/2013
(Continued)

OTHER PUBLICATIONS

English translation of the Russian Office Action dated Jul. 24, 2023 for Application No. 2021122116.
(Continued)

*Primary Examiner* — Ana L. Woodward
(74) *Attorney, Agent, or Firm* — Birch, Stewart, Kolasch & Birch, LLP

(57) ABSTRACT

Provided are: a nucleating agent for a polyolefin resin having an excellent β crystal-forming effect; a nucleating agent composition for a polyolefin resin containing the nucleating agent; a polyolefin resin masterbatch; a polyolefin resin composition; a molded article of the composition; a film of the composition; a method of producing a porous film; and a package. The nucleating agent contains a compound represented by Formula (1) below wherein M represents a monovalent to trivalent metal atom having a specific gravity of 4.0 or less, or the like; a represents 1 or 2; b represents 1 or 3; x represents an integer of 1 to 3; ax=2b is satisfied; and Z represents a group represented by Formula (2) or (3) below wherein * represents a position at which each group is linked with Z of Formula (1); Y represents a direct bond or an alkylene group having 1 to 4 carbon atoms; and $R_1$ to $R_{10}$ each independently represent a hydrogen atom, a hydroxy group, a halogen atom, an alkyl group having 1 to 10 carbon atoms, or the like.

21 Claims, No Drawings

(51) Int. Cl.
  *B29C 55/00* (2006.01)
  *B29C 55/02* (2006.01)
  *B29L 7/00* (2006.01)
  *C07C 233/63* (2006.01)
  *C07C 233/83* (2006.01)
  *C08J 3/22* (2006.01)
  *C08K 5/20* (2006.01)
  *C08L 23/14* (2006.01)

(52) U.S. Cl.
  CPC .......... *C07C 233/63* (2013.01); *C07C 233/83* (2013.01); *C08J 3/226* (2013.01); *C08K 5/20* (2013.01); *C08L 23/14* (2013.01); *B29L 2007/008* (2013.01); *C08J 2323/12* (2013.01); *C08J 2323/16* (2013.01); *C08J 2423/08* (2013.01); *C08L 2201/08* (2013.01); *C08L 2203/16* (2013.01); *C08L 2203/18* (2013.01); *C08L 2203/20* (2013.01); *C08L 2205/24* (2013.01); *C08L 2310/00* (2013.01)

(56) References Cited

U.S. PATENT DOCUMENTS

| | | |
|---|---|---|
| 9,243,123 B2 | 1/2016 | Zhao |
| 2005/0203226 A1 | 9/2005 | Mader et al. |
| 2007/0149663 A1 | 6/2007 | Schmidt et al. |
| 2011/0218279 A1 | 9/2011 | Urushihara et al. |
| 2012/0178861 A1 | 7/2012 | Nomura et al. |
| 2013/0123397 A1 | 5/2013 | Suwa et al. |
| 2015/0094406 A1 | 4/2015 | Miley et al. |
| 2019/0077761 A1 | 3/2019 | Tanaka et al. |

FOREIGN PATENT DOCUMENTS

| | | |
|---|---|---|
| CN | 103214736 A | 7/2013 |
| CN | 103289210 A | 9/2013 |
| CN | 108137505 A | 6/2018 |
| JP | 54-6038 A | 1/1979 |
| JP | 5-310665 A | 11/1993 |
| JP | 9-194650 A | 7/1997 |
| JP | 2010-53248 A | 3/2010 |
| RU | 2 318 841 C2 | 3/2008 |
| RU | 2 358 990 C2 | 6/2009 |
| RU | 2 630 221 C1 | 9/2017 |
| TW | 201224032 A1 | 6/2012 |
| TW | 201838961 A | 11/2018 |
| WO | WO 2010/024191 A1 | 3/2010 |
| WO | WO 2018/163601 A1 | 9/2018 |

OTHER PUBLICATIONS

Yu, "Relationship between the properties of substances and the structure of molecules: mathematical modeling", Successes of Contemporary Natural Science, No. 2, 2006, p. 75-76.

International Search Report for PCT/JP2019/043540 (PCT/ISA/210) mailed on Feb. 4, 2020.

Tocháček et al., "Metal-Containing Phenolic Antioxidants-Physical Behaviour and Efficiency of Stabilisation in Polypropylene", Polymer Degradation and Stability, 1990, 27 (3), pp. 297-307.

Written Opinion of the International Searching Authority for PCT/JP2019/043540 (PCT/ISA/237) mailed on Feb. 4, 2020.

Extended European Search Report for European Application No. 19904176.5, dated Jul. 18, 2022.

Ukrainczyk et al., "Interactions of salicylic acid derivatives with calcite crystals", Journal of Colloid and Interface Science, vol. 365, Sep. 7, 2011, pp. 296-307.

NUCLEATING AGENT FOR POLYOLEFIN RESIN, NUCLEATING AGENT COMPOSITION FOR POLYOLEFIN RESIN CONTAINING SAME, MASTER BATCH FOR POLYOLEFIN RESIN, POLYOLEFIN RESIN COMPOSITION, MOLDED ARTICLE THEREOF, FILM THEREOF, METHOD FOR PRODUCING POROUS FILM, AND PACKAGE

TECHNICAL FIELD

The present invention relates to: a nucleating agent for a polyolefin resin; a nucleating agent composition for a polyolefin resin, Which contains the nucleating agent; a polyolefin resin masterbatch; and a polyolefin resin composition (hereinafter, also simply referred to as "nucleating agent", "nucleating agent composition", "masterbatch" and "resin composition", respectively), as well as a molded article of the composition; a film of the composition; a method of producing a porous film; and a package. More particularly, the present invention relates to: a nucleating agent for a polyolefin resin, which has an excellent crystal-forming effect; a nucleating agent composition for a polyolefin resin, which contains the nucleating agent; a polyolefin resin masterbatch; a polyolefin resin composition; a molded article of the composition; a film of the composition; a method of producing a porous film; and a package.

BACKGROUND ART

As one of the plastic materials having the broadest application field among various thermoplastic resins that are commonly used, polyolefin resins are used in a wide range of applications because of their physical properties, moldability, cost and the like. Particularly, polyolefin resins are capable of imparting their molded articles with excellent heat resistance, transparency, impact resistance, rigidity, gas barrier properties and the like; therefore, they are expected to be utilized in various fields.

Polyolefin resins are crystalline resins that are known to form β crystals (trigonal crystals) in addition to thermodynamically most stable α crystals (monoclinic crystals) when crystallized in the presence of a specific nucleating agent. The β crystals of polyolefin resins are characterized by having, for example, a lower melting point, a lower specific gravity, a higher impact resistance, a superior stretchability and a superior heat resistance than the α crystals. As a nucleating agent that allows such polyolefin resins to preferentially form β crystals, Patent Document 1 discloses a nucleating agent containing N,N'-dicyclohexyl-2,6-naphthalene dicarboxamide.

RELATED ART DOCUMENT

Patent Document

[Patent Document 1] JPH05-310665A

SUMMARY OF THE INVENTION

Problems to be Solved by the Invention

However, the nucleating agent proposed in Patent Document 1 is not necessarily satisfactory in terms of its β crystal-forming effect, and a novel nucleating agent having an excellent β crystal-forming effect is desired at present.

In view of the above, an object of the present invention is to provide: a nucleating agent for a polyolefin resin, which has an excellent β crystal-forming effect; a nucleating agent composition for a polyolefin resin, which contains the nucleating agent; a polyolefin resin masterbatch; a polyolefin resin composition; a molded article of the composition; a film of the composition; a method of producing a porous film; and a package.

Means for Solving the Problems

The present inventors intensively studied to solve the above-described problems and consequently discovered that a specific compound containing an aspartic acid structure exhibits an excellent β crystal-forming effect on polyolefin resins, thereby completing the present invention.

That is, a nucleating agent for a polyolefin resin according to the present invention is characterized by containing a compound represented h the following Formula (1):

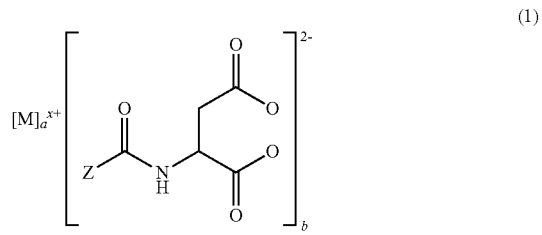

(1)

wherein M represents a monovalent to trivalent metal atom having a specific gravity of 4.0 or less, or a hydroxy group-bound divalent or trivalent metal atom having a specific gravity of 4.0 or less; a represents 1 or 2; b represents 1 or 3; x represents an integer of 1 to 3; ax=2b is satisfied; and Z represents a group represented by the following Formula (2) or (3):

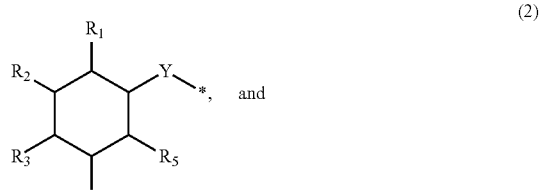

(2)

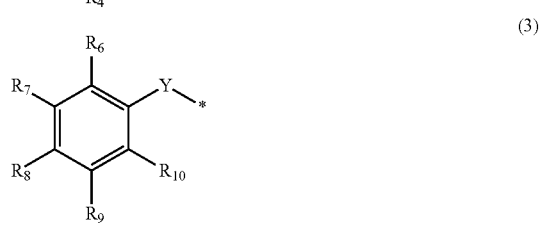

(3)

wherein * represents a position at which each group is linked with Z of Formula (I); Y represents a direct bond or an alkylene group having 1 to 4 carbon atoms; and $R_1$ to $R_{10}$ each independently represent a hydrogen atom, a hydroxy group, a halogen atom, an alkyl group having 1 to 10 carbon atoms, a halogenated alkyl group having 1 to 10 carbon atoms, an alkoxy group having 1 to 10 carbon atoms, or an alkenyl group having 2 to 10 carbon atoms.

In the nucleating agent of the present invention, M is preferably lithium, sodium, potassium, magnesium, calcium, barium, aluminum, hydroxyaluminum, or dihydroxyaluminum.

A nucleating agent composition for a polyolefin resin according to the present invention is characterized by containing: the nucleating agent for a polyolefin resin according to the present invention; and at least one additive selected from the group consisting of a phenolic antioxidant, a phosphorus-based antioxidant, a sulfur-based antioxidant, other antioxidant, a hindered amine compound, an ultraviolet absorber, a nucleating agent different from the compound represented by Formula (1), a flame retardant, a flame retardant aid, a lubricant, a filler, a hydrotalcite, a fatty acid metal salt, an antistatic agent, a fluorescent brightener, a pigment, and a dye.

Further, a polyolefin resin masterbatch of the present invention is characterized by containing: a polyolefin resin; and the nucleating agent for a polyolefin resin according to the present invention.

Still further, a polyolefin resin composition of the present invention contains: a polyolefin resin; and the nucleating agent for a polyolefin resin according to the present invention, the composition being characterized in that a content of the nucleating agent for a polyolefin resin is 0.001 to 10 parts by mass with respect to 100 parts by mass of the polyolefin resin.

In the resin composition of the present invention, the polyolefin resin is preferably a polypropylene resin. Further, in the resin composition of the present invention, the polyolefin resin preferably contains an ethylene-propylene copolymer. The resin composition of the present invention preferably further contains an elastomer. Moreover, the resin composition of the present invention preferably further contains a filler.

A molded article of the present invention is characterized by containing the polyolefin resin composition of the present invention.

The molded article of the present invention is preferably an automotive exterior component, an automotive interior component, a housing, a container, or a pipe.

A film of the present invention is characterized by containing the polyolefin resin composition of the present invention.

The film of the present invention is preferably a porous film containing voids, and is suitable as a light reflection film or a battery separator.

A method of producing a porous film according to the present invention includes: a molding step of molding a polyolefin resin composition to obtain a film; and a step of heat-stretching the film obtained by the molding step, the method being characterized in that the polyolefin resin composition is the polyolefin resin composition of the present invention.

A package of the present invention is characterized by containing the film of the present invention.

Effects of the Invention

According to the present invention, a nucleating agent for a polyolefin resin, which has an excellent β crystal-forming effect; a nucleating agent composition for a polyolefin resin, which contains the nucleating agent; a polyolefin resin masterbatch; a polyolefin resin composition; a molded article of the composition; a film of the composition; a method of producing a porous film; and a package can be provided.

MODE FOR CARRYING OUT THE INVENTION

Embodiments of the present invention will now be described in detail. First, the nucleating agent for a polyolefin resin according to the present invention will be described.

<Nucleating Agent for Polyolefin Resin>

The nucleating agent for a polyolefin resin according to the present invention contains a compound represented by the following Formula (1) and has an excellent β crystal-forming effect.

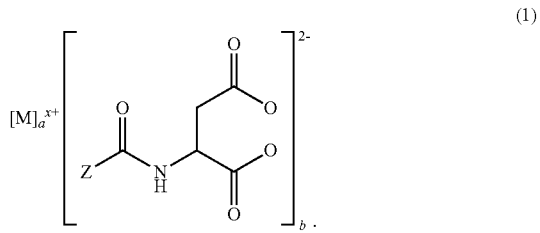

(1)

In Formula (1), M represents a monovalent to trivalent metal atom having a specific gravity of 4.0 or less, or a hydroxy group-bound divalent or trivalent metal atom having a specific gravity of 4.0 or less; a represents 1 or 2; b represents 1 or 3; x represents an integer of 1 to 3; ax=2b is satisfied; and Z represents a group represented by the following Formula (2) or (3):

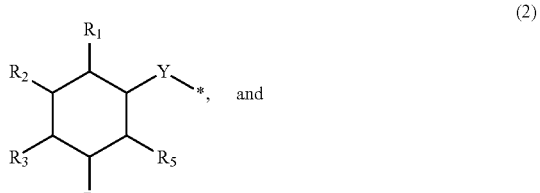

(2)

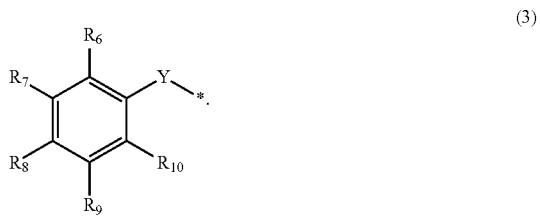

(3)

In Formulae (2) and (3), * represents a position at which each group is linked with Z of Formula (1); Y represents a direct bond or an alkylene group having 1 to 4 carbon atoms; and $R_1$ to $R_{10}$ each independently represent a hydrogen atom, a hydroxy group, a halogen atom, an alkyl group having 1 to 10 carbon atoms, a halogenated alkyl group having 1 to 10 carbon atoms, an alkoxy group having 1 to 10 carbon atoms, or an alkenyl group having 2 to 10 carbon atoms.

In Formulae (2) and (3), examples of the alkylene group having 1 to 4 carbon atoms represented by Y include a methylene group, an ethylene, a propylene group, a butylene group, and an isobutylene group. From the standpoint of attaining an excellent β crystal-forming effect, Y is preferably a direct bond or a methylene group.

In Formulae (2) and (3), examples of the halogen atom represented by $R_1$ to $R_{10}$ include fluorine, chlorine, bromine, and iodine. Thereamong, chlorine is particularly preferred.

In Formulae (2) and (3), examples of the alkyl group having 1 to 10 carbon atoms represented by $R_1$ to $R_{10}$ include linear or branched alkyl groups, and cycloalkyl groups having 3 to 10 carbon atoms. Specific examples thereof a methyl group, an ethyl group, an n-propyl group, an isopropyl group, a cyclopropyl group, an n-butyl group, a sec-butyl group, a tort-butyl group, an isobutyl group, a cyclobutyl group, an n-amyl group, a tert-amyl group, a cyclopentyl group, an n-hexyl group, a cyclohexyl group, an n-heptyl group, a cycloheptyl group, an n-octyl group, an isooctyl group, a tert-octyl group, a 2-ethylhexyl group, an n-nonyl group, an isononyl group, and an n-decyl group.

In Formulae (2) and (3), examples of the halogenated alkyl group having 1 to 10 carbon atom represented by $R_1$ to $R_{10}$ include the above-exemplified alkyl groups in which some or all of hydrogen atoms are each substituted with a halogen atom, and examples of the halogen atom include fluorine, chlorine, bromine, and iodine.

In Formulae (2) and (3), examples of the alkoxy group having 1 to 10 carbon atoms represented by $R_1$ to $R_{10}$ include linear or branched alkoxy groups, and cycloalkoxy groups having 5 to 10 carbon atoms. Specific examples thereof include a methoxy group, an ethoxy group, an n-propoxy group, an n-butoxy group, an n-hexyloxy group, a 1-methylethoxy group, a 2-methylpropoxy group, a 1-methylbutoxy group, a 4-methylpentyloxy group, and a cyclohexyloxy group.

In Formulae (2) d (3), examples of the alkenyl group having 2 to 10 carbon atoms represented by $R_1$ to $R_{10}$ include vinyl, propenyl, butenyl, hexenyl, octenyl, and decenyl. The double bond thereof may be located internally or at the α- or ω-position.

In Formulae (2) and (3), $R_1$ to $R_{10}$ are each preferably a hydrogen atom or a halogen atom, particularly preferably a hydrogen atom.

In Formula (1), examples of M include metal atoms, such as lithium, sodium, potassium, magnesium, calcium, barium, and aluminum. The divalent or trivalent metal atoms may be hound with a hydroxy group. Examples of the hydroxy group-bound divalent to trivalent metal atom include hydroxyaluminum and dihydroxyaluminum From the standpoint of obtaining a nucleating agent that has an excellent β crystal-forming effect, M in Formula (1) is preferably lithium, sodium, potassium, magnesium, calcium, barium, aluminum, hydroxyaluminum or dihydroxyaluminum, more preferably lithium, sodium, potassium, calcium or hydroxyaluminum, particularly sodium.

In Formula (1), b is preferably 1, and x is preferably 1 or 2.

In Formula (1), Z is preferably a group represented by Formula (3). In this case, the nucleating agent of the present invention exhibits a superior β crystal-forming effect.

Specific examples of the compound represented by Formula (1) include the followings. However, the nucleating agent of the present invention is not restricted thereto.

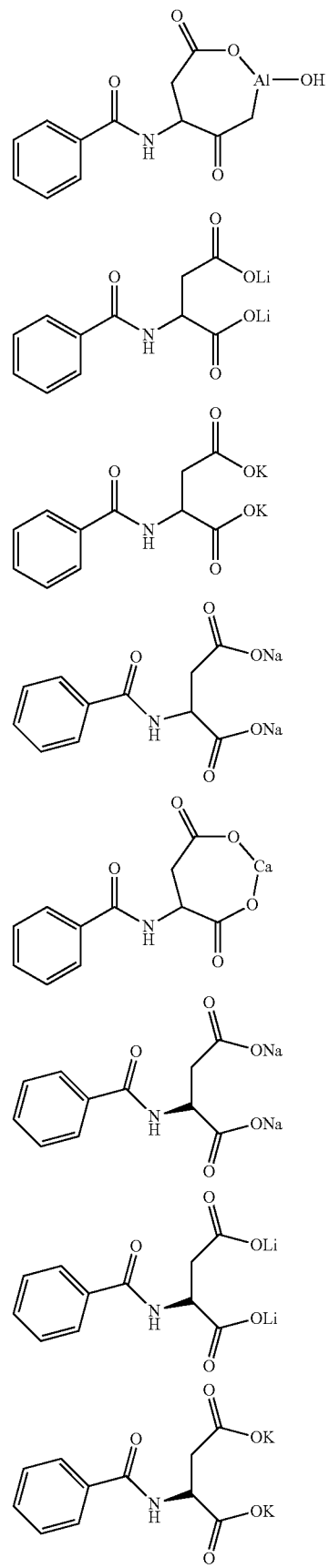

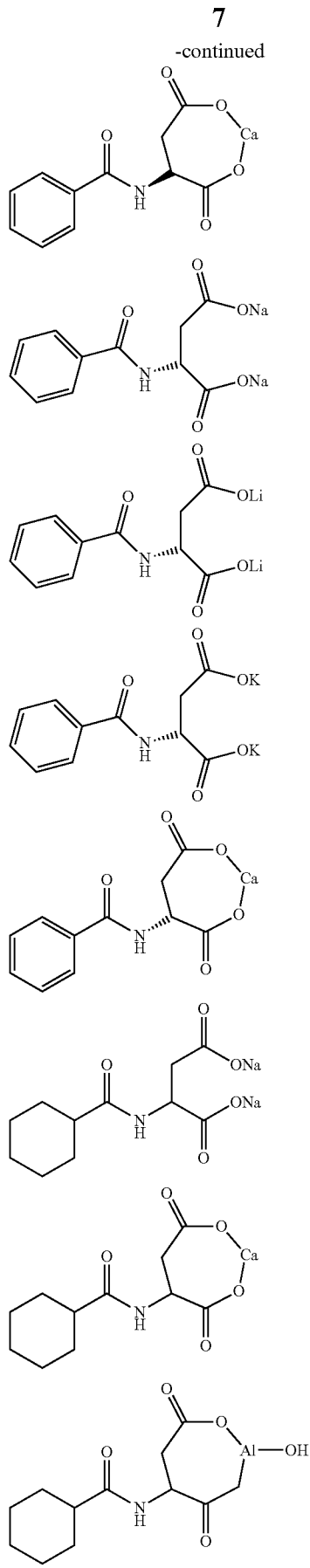
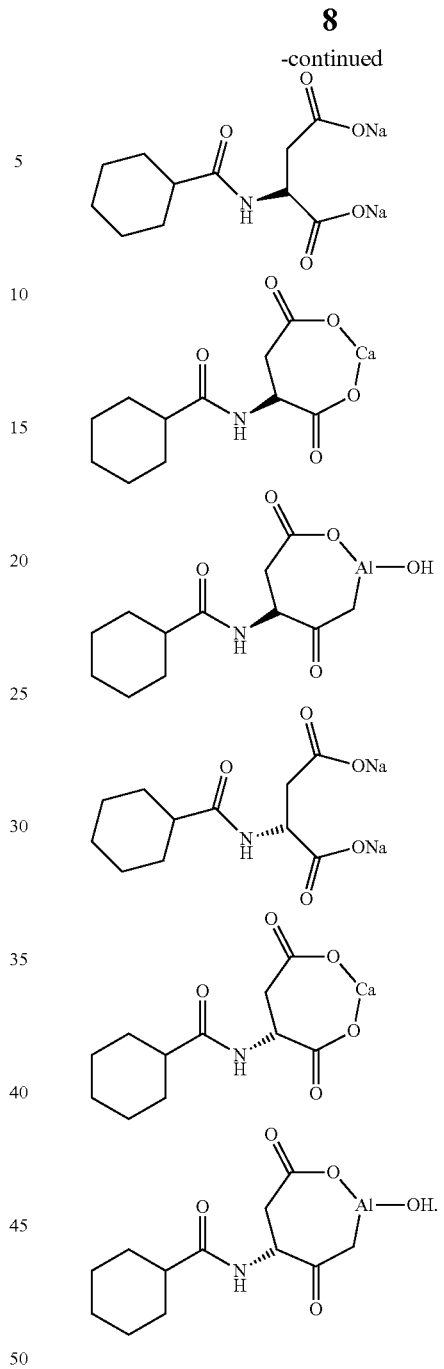

The compound represented by Formula (1) can be produced by, for example, a method of allowing a metal salt of aspartic acid to react with a carboxylic acid chloride, such as benzoic acid chloride or cyclohexane carboxylic acid chloride, in the presence of a base.

<Nucleating Agent Composition for Polyolefin Resin>

Next, embodiments of the nucleating agent composition for a polyolefin resin according to the present invention will be described. The nucleating agent composition of the present invention contains: the nucleating agent of the present invention; and at least one additive selected from the group consisting of a phenolic antioxidant, a phosphorus-based antioxidant, a sulfur-based antioxidant, other antioxidant, a hindered amine compound, an ultraviolet absorber, a nucleating agent different from the compound represented by Formula (1), a flame retardant, a flame retardant aid, a lubricant, a filler, a hydrotalcite, a fatty acid metal salt, an antistatic agent, a fluorescent brightener, a pigment, and a dye. The nucleating agent composition of the present invention exhibits an excellent β crystal-forming effect.

Examples of the phenolic antioxidant include 2,6-di-tert-butyl-4-ethylphenol, 2-tert-butyl-4,6-dimethylphenol, styrenated phenol, 2,2'-methylene-bis(4-ethyl-6-Cert-butylphenol), 2,2'-thiobis-(6-tert-butyl-4-methylphenol), 2,2'-thiodiethylene-bis[3-(3,5-di-tert-butyl-4-hydroxyphenyl) propionate], 2-methyl-4,6-bis(octylsulfanylmethyl)phenol, 2,2'-isobutylidene-bis(4,6-dimethylphenol), isooctyl-3-(3,5-di-tert-butyl-4-hydroxyphenyl)propionate, N,N'-hexane-1,6-diylbis[3-(3,5-di-tert-butyl-4-hydroxyphenyl)propionamide], 2,2'-oxamide-bis[ethyl-3-(3,5-di-tert-butyl-4-hydroxyphenyl)propionate], 2-ethylhexyl-3-(3',5'-di-tert-butyl-4'-hydroxyphenyl)propionate, 2,2'-ethylene-bis(4,6-di-text-butylphenol), esters of 3,5-di-tert-butyl-4-hydroxybenzenepropanoic acid and a C13-15 alkyl, 2,5-di-tert-amylhydroquinone, hindered phenol polymers (e.g., trade name "AO.OH.98" manufactured by ADEKA Polymer Additives Europe SAS), 2,2'-methyl ene-bis[6-(1-methylcyclohexyl)-p-cresol], 2-tert-butyl-6-(3-tert-butyl-2-hydroxy-5-methyl)-4-methylphenyl acrylate, 2-[1-(2-hydroxy-3,5-di-tert-pentylphenyl)ethyl]-4,6-di-tert-pentyl phenyl acrylate, 6-[3-(3-tert-butyl-4-hydroxy-5-methyl)propoxy]-2,4,8,10-tetra-tert-butylbenzo[d,f][1,3,2]-dioxaphosphepin, hexamethylene-bis[3-(3,5-di-tert-butyl-4-hydroxyphenyl)propionate, calcium bis[monoethyl(3,5-di-tert-butyl-4-hydroxybenzyl)phosphonate], a reaction product between 5,7-bis(1,1-dimethylethyl)-3-hydroxy-2(3H)-benzofuranone and o-xylene, 2,6-di-tert-butyl-4-(4,6-bis(octylthio)-1,3,5-triazine-2-ylamino)phenol, DL-α-tocophenol (vitamin E), 2,6-bis(α-methylbenzyl)-4-methylphenol, bis[3,3-bis-(4'-hydroxy-3'-tert-butyl-phenyl)butyric acid]glycol ester, 2,6-di-tert-butyl-p-cresol, 2,6-diphenyl-4-octadecyloxyphenol, stearyl(3,5-di-tert-butyl-4-hydroxyphenyl)propionate, distearyl(3,5-di-tert-butyl-4-hydroxybenzyl)phosphonate, tridecyl-3,5-tert-butyl-4-hydroxybenzyl thioacetate, thiodiethylene-bis[(3,5-di-tert-butyl-4-hydroxyphenyl)propionate], 4,4'-thiobis(6-tert-butyl-m-cresol), 2-octylthio-4,6-di(3,5-di-tert-butyl-4-hydroxyphenoxy)-s-triazine, 2,2'-methylene-bis(4-methyl-6-tort-butylphenol), bis[3,3-bis(4-hydroxy-3-tert-butylphenyl)butyric acid]glycol ester, 4,4'-butylidene-bis(2,6-di-tert-butylphenol), 4,4'-butylidene-bis(6-tort-butyl-3-methylphenol), 2,2'-ethylidene-bis(4,6-di-tert-butylphenol), 1,1,3-tris(2-methyl-4-hydroxy-5-tert-butylphenyl)butane, bis[2-tert-butyl-4-methyl-6-(2-hydroxy-3-tert-butyl-5-methylbenzyl)phenyl]terephthalate, 1,3,5-tris(2,6-dimethyl-3-hydroxy-4-tert-butylbenzyl)isocyanurate, 1,3,5-tris(3,5-di-tert-butyl-4-hydroxybenzyl)isocyanurate, 1,3,5-tris(3,5-di-text-butyl-4-hydroxybenzyl)-2,4,6-trimethylbenzene, 1,3,5-tris[(3,5-di-tert-butyl-4-hydroxyphenyl)propionyloxyethyl]isocyanurate, tetrakis[methylene-3-(3',5'-tert-butyl-4'-hydroxyphenyl)propionate]methane, 2-tert-butyl-4-methyl-6-(2-acryloyloxy-3-tert-butyl-5-methylbenzyl)phenol, 3,9-bis[2-(3-tert-butyl-4-hydroxy-5-methylhydrocinnamoyloxy)-1,1-dimethylethyl]-2,4,8,10-tetraoxaspiro[5.5]undecane, triethylene glycol-bis[β-(3-tert-butyl-4-hydroxy-5-methylphenyl)propionate], and 3-(3,5-dialkyl-4-hydroxyphenyl)propionic acid derivatives, such as stearyl-3-(3,5-di-tert-butyl-4-hydroxyphenyl) propionic acid amide, palmityl-3-(3,5-di-tert-butyl-4-hydroxyphenyl)propionic acid amide, myristyl-3-(3,5-di-test-butyl-4-hydroxyphenyl)propionic acid amide and lauryl-3-(3,5-di-tert-butyl-4-hydroxyphenyl)propionic acid amide. These phenolic antioxidants may be used individually or two or more thereof may be used in combination. In cases where the nucleating agent composition of the present invention contains a phenolic antioxidant, the content of the phenolic antioxidant may be adjusted such that it is 0.001 to 5 parts by mass with respect to 100 parts by mass of a polyolefin resin when the nucleating agent composition of the present invention is incorporated into the polyolefin resin.

Examples of the phosphorus-based antioxidant include triphenyl phosphite, diisooctyl phosphite, heptakis(dipropylene glycol)triphosphite, triisodecyl phosphite, diphenylisooctyl phosphite, diisooctylphenyl phosphite, diphenyltridecyl phosphite, triisooctyl phosphite, trilauryl phosphite, diphenyl phosphite, tris(dipropylene glycol)phosphite, dioleyl hydrogen phosphite, trilauryl trithiophosphite, bis(tridecyl)phosphite, tris(isodecyl)phosphite, tris(tridecyl)phosphite, diphenyldecyl phosphite, dinonylphenyl-bis(nonylphenyl)phosphite, poly(dipropylene glycol)phenyl phosphite, tetraphenyldipropyl glycol diphosphite, trisnonylphenyl phosphite, tris(2,4-di-tert-butylphenyl)phosphite, tris(2,4-di-tert-butyl-5-methylphenyl)phosphite, tris[2-tert-butyl-4-(3-tert-butyl-4-hydroxy-5-methylphenylthio)-5-methylphenyl]phosphite, tri(decyl) phosphite, octyldiphenyl phosphite, di(decyl)monophenyl phosphite, mixtures of distearyl pentaerythritol and calcium stearate, alkyl(C10) bisphenol-A phosphite, tetraphenyl-tetra(tridecyl)pentaerythritol tetraphosphite, bis(2,4-di-tert-butyl-6-methylphenyl) ethyl phosphite, tetra(tridecyl)isopropylidene diphenol diphosphite, tetra(tridecyl)-4,4'-n-butylidene-bis(2-tert-butyl-5-methylphenol)diphosphite, hexa(tridecyl)-1,1,3-tris(2-methyl-4-hydroxy-5-tert-butylphenyl)butane triphosphite, tetrakis(2,4-di-tert-butylphenyl)biphenylene diphosphonite, 9,10-dihydro-9-oxa-10-phospha-phenanthrene-10-oxide, (1-methyl-1-propenyl-3-ylidene) tris(1,1-dimethylethyl)-5-methyl-4,1-phenylene)hexatridecyl phosphite, 2,2'-methylene-bis(4,6-di-tert-butylphenyl)-2-ethylhexyl phosphite, 2,2'-methylene-bis(4,6-di-tert-butylphenyl)-octadecyl phosphite, 2,2'-ethylidene-bis(4,6-di-tert-butylphenyl)fluorophosphite, 4,4'-butylidene-bis(3-methyl-6-tert-butylphertylditridecyl) phosphite, tris(2-[(2,4,8,10-tetrakis-tert-butyldibenzo[d,f][1,3,2]dioxaphosphepin-6-yl)oxy]ethyl)amine, 3,9-bis(4-nonylphenoxy)-2,4,8,10-tetraoxa-3,9-diphosphespiro[5.5]undecane, 2,4,6-tri-tert-butylphenyl-2-butyl-2-ethyl-1,3-propanediol phosphite, poly-4,4'-isopropylidene diphenol C12-15 alcohol phosphite, bis(diisodecyl)pentaerythritol diphosphite, bis(tridecyl)pentaerythritol diphosphite, bis(octadecyl)pentaerythritol diphosphite, bis(nonylphenyl)pentaerythritol diphosphite, bis(2,4-di-tert-butylphenyl)pentaerythritol diphosphite, bis(2,4,6-tri-tert-butylphenyl)) pentaerythritol diphosphite, bis(2,6-di-tert-butyl-4-methylphenyl)pentaerythritol diphosphite, and bis(2,4-dicumylphenyl)pentaerythritol diphosphite. These phosphorus-based antioxidants may be used individually, or two or more thereof may be used in combination. In cases where the nucleating agent composition of the present invention contains a phosphorus-based antioxidant, the content of the phosphorus-based antioxidant may be adjusted such that it is 0.001 to 5 parts by mass with respect to 100 parts by mass of a polyolefin resin when the nucleating agent composition of the present invention is incorporated into the polyolefin resin.

Examples of the sulfur-based antioxidant include tetrakis[methylene-3-(laurylthio)propionate]methane, bis(methyl-4-[3-n-alkyl(C12/C14)thiopropionyl oxy]-5-tert-butylphenyl)sulfide, ditridecyl-3,3'-thiodipropionate, dilauryl-3,3'-thiodipropionate, dimyristyl-3,3'-thiodipropionate, distearyl-3,3'-thiodipropionate, lauryl/stearyl thiodipropionate, 4,4'-thiobis(6-tert-butyl-m-cresol), 2,2'-thiobis(6- text-butyl-p-cresol), and distearyl disulfide. These sulfur-based antioxidants may be used individually, or two or more thereof may be used in combination. In cases where the nucleating agent composition of the present invention contains a sulfur-based antioxidant, the content of the sulfur-based antioxidant may be adjusted such that it is 0.001 to 10 parts by mass with respect to 100 parts by mass of a polyolefin resin when the nucleating agent composition of the present invention is incorporated into the polyolefin resin.

Examples of the above-described other antioxidant include nitrone compounds, such as N-benzyl-α-phenyl nitrone, N-ethyl-α-methyl nitrone, N-octyl-α-heptyl nitrone, N-lauryl-α-undecyl nitrone, N-tetradecyl-α-tridecyl nitrone, N-hexadecyl-α-pentadecyl nitrone, N-octyl-α-heptadecyl nitrone, N-hexadecyl-α-heptadecyl nitrone, N-octadecyl-α-pentadecyl nitrone, N-heptadecyl-α-heptadecyl nitrone, and N-octadecyl-α-heptadecyl nitrone; and benzofuran compounds, such as 3-arylbenzofuran-2(3H)-one, 3-(alkoxyphenyl)benzofuran-2-one, 3-(acyloxyphenyl)benzofuran-2(3H)-one, 5,7-di-tert-butyl-3-(3,4-dimethylphenyl)-benzofuran-2(3H)-one, 5,7-di-tert-butyl-3-(4-hydroxyphenyl)-benzofuran-2(3H)-one, 5,7-di-tert-butyl-3-{4-(2-hydroxyethoxy)phenyl}-benzofuran-2(3H)-one, 6-(2-(4-(5,7-di-tert-2-oxo-2,3-dihydrobenzofuran-3-yl)phenoxy)ethoxy)-6-oxohexyl-6-((6-hydroxyhexanoyl)oxy) hexanoate, and 5-di-tert-butyl-3-(4-((15-hydroxy-3,6,9,13-tetraoxapentadecyl)oxy)phenyl)benzofuran-2(3H)-one. These other antioxidants may be used individually, or two or more thereof may be used in combination. In cases where the nucleating agent composition of the present invention contains other antioxidant, the content of the other antioxidant may be adjusted such that it is 0.001 to 20 parts by mass respect to 100 parts by mass of a polyolefin resin when the nucleating agent composition of the present invention is incorporated into the polyolefin resin.

Examples of the hindered amine compound include 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl)sebacate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl)-di(tridecyl)-1,2,3,4-butanetetracarboxylate, bis(1,2,2,6,6-pentamethyl-4-piperidyl).di(tridecyl)-1,2,3,4-butanetetracarboxylate, bis(1,2,2,4,4-pentamethyl-4-piperidyl)-2-butyl-2-(3,5-di-tert-butyl-4-hydroxybenzyl)malonate, 1-(2-hydroxyethyl)-2,2,6,6-tetramethyl-4-piperidinol/diethyl succinate polycondensate, 1,6-bis(2,2,6,6-tetramethyl-4-piperidylamino)hexane/2,4-dichloro-6-morpholino-s-triazine polycondensate, 1,6-bis(2,2,6,6-tetramethyl-4-piperidylamino) hexane/2,4-dichloro-6-tert-octyl amino-s-triazine polycondensate, 1,5,8,12-tetrakis[2,4-bis(N-butyl-N-(2,2,6,6-tetramethyl-4-piperidyl)amino)-s-triazine-6-yl]-1,5,8,12-tetraazadodecane, 1,5,8,12-tetrakis[2,4-bis(N-butyl-N-(1,2,2,6,6-pentamethyl-4-piperidyl)amino)-s-triazine-6-yl]-1,5,8,12-tetraazadodecane, 1,6,11-tris[2,4-bis(N-butyl-N-(2,2,6,6-tetramethyl-4-piperidyl)amino)-s-triazine-6-yl] aminoundecane, 1,6,11-tris[2,4-bis(N-butyl-N-(1,2,2,6,6-pentamethyl-4-piperidyl)amino)-s-triazine-6-yl]amino undecane, bis{4-(1-octyloxy-2,2,6,6-tetramethyl) piperidyl}decanedionate, and bis{4-(2,2,6,6-tetramethyl-1-undecyloxy)piperidyl)carbonate. These hindered amine compounds may be used individually, or two or more thereof may be used in combination. In cases where the nucleating agent composition of the present invention contains a hindered amine compound, the content of the hindered amine compound may be adjusted such that it is 0.001 to 20 parts by mass with respect to 100 parts by mass of a polyolefin resin when the nucleating agent composition of the present invention is incorporated into the polyolefin resin.

Examples of the ultraviolet absorber include 2-hydroxybenzophenones, such as 2,4-dihydroxybenzophenone and 5,5'-methylene-bis(2-hydroxy-4-methoxybenzophenone); 2-(2-hydroxyphenyl)benzotriazoles, such as 2-(2-hydroxy-5-methylphenyl)benzotriazole, 2-(2-hydroxy-5-tert-octylphenyl)benzotriazole, 2-(2-hydroxy-3,5-di-tert-butylphenyl)-5-chlorobenzotriazole, 2-(2-hydroxy-3-tert-butyl-5-methylphenyl)-5-chlorobenzotriazole, 2-(2-hydroxy-3,5-dicumylphenyl)benzotriazole, 2,2'-methylene-bis(4-tert-octyl-6-benzotriazolylphenol), polyethylene glycol esters of 2-(2-hydroxy-3-cert-butyl-5-carboxyphenyl)benzotriazole, 2-[2-hydroxy-3-(2-acryloyloxyethyl)-5-methylphenyl]benzotriazole, 2-[2-hydroxy-3-(2-methacryloyloxyethyl)-5-tert-butylphenyl]benzotriazole, 2-[2-hydroxy-3-(2-methacryloyloxyethy)-5-tert-octylphenyl]benzotriazole, 2-[2-hydroxy-3-(2-methacryloyloxyethyl)-5-tert-butylphenyl]-5-chlorobenzotriazole, 2-[2-hydroxy-5-(2-methacryloyloxyethyl)phenyl]benzotriazole, 2-[2-hydroxy-3-tert-butyl-5-(2-methacryloyloxyethyl)phenyl] benzotriazole, 2-[2-hydroxy-3-tert-amyl-5-(2-methacryloyloxyethy)phenyl]benzotriazole, 2-[2-hydroxy-3-tert-butyl-5-(3-methacryloyloxypropyl)phenyl]-5-chlorobenzotriazole, 2-[2-hydroxy-4-(2-methacryloyloxymethyl)phenyl]benzotriazole, 2-[2-hydroxy-4-(3-methacryloyloxy-2-hydroxypropyl)phenyl] benzotriazole, and 2-[2-hydroxy-4-(3-methacryloyloxypropyl)phenyl]benzotriazole; benzoates, such as phenyl salicylate, resorcinol monobenzoate, 2,4-di-tert-butylphenyl-3,5-di-tert-butyl-4-hydroxybenzoate, octyl (3,5-di-tert-butyl-4-hydroxy)benzoate, dodecyl(3,5-di-tert-butyl-4-hydroxy)benzoate, tetradecyl(3,5-di-tert-butyl-4-hydroxy)benzoate, hexadecyl(3,5-di-tert-butyl-4-hydroxy) benzoate, octadecyl(3,5-di-tert-butyl-4-hydroxy)benzoate, and behenyl(3,5-di-tert-butyl-4-hydroxy)benzoate; substituted oxanilides, such as 2-ethyl-2'-ethoxyoxanilide and 2-ethoxy-4'-dodecyloxanilide; cyanoacrylates, such as ethyl-α-cyano-β,β-diphenyl acrylate and methyl-2-cyano-3-methyl-3-(p-methoxyphenyl)acrylate; triazines, such as 2-(4,6-diphenyl-1,3,5-triazine-2-yl)-5-hexyloxyphenol, 2-(2-hydroxy-4-octoxyphenyl)-4,6-bis(2,4-dimethylphenyl)-1,3,5-triazine, trioctyl-2,2',2"-((1,3,5-triazine-2,4,6-triyl)tris(3-hydroxybenzene-4-,1-diyl)tripropionate), 2-(4,6-diphenyl-1,3,5-triazine-2-yl)-5-[2-(2-ethylhexanoyloxy) ethoxy]phenol, 2,4,6-tris(2-hydroxy-4-hexyloxy-3-methylphenyl)-1,3,5-triazine, and 1,12-bis[2-[4-(4,6-diphenyl-1,3,5-triazine-2-yl)-3-hydroxyphenoxy]ethyl] dodecane dioate; and a variety of metal salts and metal chelates, particularly salts and chelates of nickel and chromium. These ultraviolet absorbers may be used individually, or two or more thereof may be used in combination. In cases where the nucleating agent composition of the present invention contains an ultraviolet absorber, the content of the ultraviolet absorber may be adjusted such that it is 0.001 to 20 parts by mass with respect to 100 parts by mass of a polyolefin resin when the nucleating agent composition of the present invention is incorporated into the polyolefin resin.

Examples of the above-described other nucleating agent different from the compound represented by Formula (1) include metal carboxylates, such as sodium-2,2'-methylene-bis(4,6-di-tert-butylphenyl)phosphate, lithium-2,2'-methylene-bis(4,6-di-tert-butylphenyl)phosphate, aluminum hydroxybis[2,2'-methylene-bis(4,6-di-tert-butylphenyl) phosphate], sodium benzoate, 4-tert-butylbenzoate aluminum salt, sodium adipate, 2-sodium-bicyclo[2.2.1]heptane-2,3-dicarboxylate, and calcium cyclohexane-1,2-dicarboxylate; polyol derivatives, such as dibenzylidene sorbitol, bis(methylbenzylidene)sorbitol, bis(3,4-dimethylbenzylidene)sorbitol, bis(p-ethylbenzylidene)sorbitol, bis(dimethylbenzylidene)sorbitol, and 1,2,3-trideoxy 4,6:5,7-bis-O-((4-propylphenyl)methylene)nonitol; and amide compounds, such as N,N',N''-tris[2-methylcyclohexyl]-1,2,3-propane tricarboxamide, N,N',N''-tricyclohexyl-1,3,5-benzene tricarboxamide, N,N'-dicyclohexylnaphthalene dicarboxamide, and 1,3,5-tri(dimethylisopropoylamino) benzene. These other nucleating agents may be used individually, or two or more thereof may be used in combination. In cases where the nucleating agent composition of the present invention contains other nucleating agent different from the compound represented by Formula (1), the content of the other nucleating agent may be adjusted such that it is 0.001 to 10 parts by mass with respect to 100 parts by mass of a polyolefin resin when the nucleating agent composition of the present invention is incorporated into the polyolefin resin.

Examples of the flame retardant include aromatic phosphates, such as triphenyl phosphate, tricresyl phosphate, trixylenyl phosphate, cresyldiphenyl phosphate, cresyl-2,6-dixylenyl phosphate, resorcinol-bis(diphenylphosphate), (1-methylethylidene)-4,1-phenylene tetraphenyl diphosphate, and 1,3-phenylene-tetrakis(2,6-dimethylphenyl)phosphate, as well as "ADK STAB FP-500", "ADK STAB FP-600" and "ADK STAB FP-800" (trade names, manufactured by ADEKA Corporation); phosphonates, such as divinyl phenylphosphonate, diallyl phenylphosphonate, and (1-butenyl) phenylphosphonate; phosphinates, such as phenyl diphenylphosphinate, methyl diphenylphosphinate, and 9,10-dihydro-9-oxa-10-phosphaphenanthlene-10-oxide derivatives; phosphazene compounds, such as bis(2-allylphenoxy)phosphazene and dicresyl phosphazene; phosphorus-based flame retardants, such as melamine phosphate, melamine pyrophosphate, melamine polyphosphate, melam polyphosphate, an polyphosphate, piperazine phosphate, piperazine pyrophosphate, piperazine polyphosphate, phosphorus-containing vinylbenzyl compounds, and red phosphorus; metal hydroxides, such as magnesium hydroxide and aluminum hydroxide; and bromine-based flame retardants, such as brominated bisphenol A-type epoxy resins, brominated phenol novolac-type epoxy resins, hexabromobenzene, pentabromotoluene, ethylene-bis(pentabromophenyl), ethylene-bis-tetrabromophthalimide, 1,2-dibromo-4-(1,2-dibromoethyl)cyclohexane, tetrabromocyclooctane, hexabromocyclododecane, bis(tribromophenoxy)ethane, brominated polyphenylene ether, brominated polystyrene, 2,4,6-tris(tribromophenoxy)-1,3,5-triazine, tribromophenyl maleimide, tribromophenyl acrylate, tribromophenyl methacrylate, tetrabromobisphenol A-type dimethacrylate, pentabromobenzyl acrylate, and brominated styrene. These flame retardants are preferably used in combination with a drip inhibitor such as a fluorocarbon resin, and/or a flame retardant aid such as a polyhydric alcohol or hydrotalcite. These flame retardants may be used individually, or two or more thereof may be used in combination. In cases where the nucleating agent composition of the present invention contains a flame retardant, the content of the flame retardant may be adjusted such that it is 1 to 100 parts by mass with respect to 100 parts by mass of a polyolefin resin when the nucleating agent composition of the present invention is incorporated into the polyolefin resin.

The lubricant is added for the purposes of imparting the surface of the resulting molded article with lubricity and improving the damage-preventing effect. Examples of the lubricant include unsaturated fatty acid amides, such as oleic acid amide and erucic acid amide; saturated fatty acid amides, such as behenic acid amide and stearic acid amide; butyl stearate; stearyl alcohols; stearic acid monoglyceride; sorbitan monopalmitate; sorbitan monostearate; mannitol; stearic acid; hardened castor oil; stearic acid amide; oleic acid amide; and ethylene-bis stearic acid amide. These lubricants may be used individually, or two or more thereof may be used in combination. In cases where the nucleating agent composition of the present invention contains a lubricant, the content of the lubricant may be adjusted such that it is 0.01 to 2 parts by mass with respect to 100 parts by mass of a polyolefin resin when the nucleating agent composition of the present invention is incorporated into the polyolefin resin.

Examples of the filler include talc, mica, calcium carbonate, calcium oxide, calcium hydroxide, magnesium carbonate, magnesium hydroxide, magnesium oxide, magnesium sulfate, aluminum hydroxide, barium sulfate, glass powder, glass fibers, clays, dolomite, silica, alumina, potassium titanate whiskers, wollasionite, and fibrous magnesium oxysulfate, and any of these fillers can be used by appropriately selecting the particle size (the fiber diameter, fiber length and aspect ratio in the case of a fibrous filler). Among these fillers, talc is particularly preferably used since it can impart especially excellent rigidity to the resulting molded article and can be easily obtained. Further, the filler to be used may be subjected to a surface treatment as required. The above-described fillers may be used individually, or two or more thereof may be used in combination. In cases where the nucleating agent composition of the present invention contains a filler, the content of the filler may be adjusted such that it is 0.01 to 80 parts by mass with respect to 100 parts by mass of a polyolefin resin when the nucleating agent composition of the present invention is incorporated into the polyolefin resin.

The fatty acid metal salt is preferably a compound represented by the following Formula (4) from the standpoint of attaining heat resistance and dispersion effect of the nucleating agent in a resin.

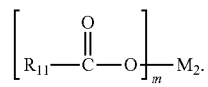

(4)

In Formula (4), $R_{11}$ represents a linear or branched fatty acid residue having 12 to 20 carbon atoms, the fatty acid residue may be substituted with a hydroxy group, $M_2$ represents a monovalent to trivalent metal atom which may be hound with a hydroxy group, and in represents an integer of 1 to 3.

In cases where the nucleating agent composition of the present invention contains a fatty acid metal salt, the content of the fatty acid metal salt may be adjusted such that it is 0.001 to 10 parts by mass with respect to 100 parts by mass of a polyolefin resin when the nucleating agent composition of the present invention is incorporated into the polyolefin resin.

In Formula (4), specific examples of $M_2$ include sodium, potassium, lithium, calcium, zinc, barium, magnesium and hydroxyaluminum, among which sodium, potassium and lithium are particularly preferred.

The above-described hydrotalcite is a complex salt compound which is known as a natural or synthetic product and composed of magnesium, aluminum, hydroxy groups, a carbonate group and arbitrary crystal water, and examples thereof include hydrotalcites in which some of the magnesium or aluminum atoms are substituted with other metal such as an alkali metal or zinc; and hydrotalcites in which the hydroxy group(s) and/or carbonate group is/are substituted with other anionic group(s), specifically hydrotalcites represented by the following Formula (5) in which a metal is substituted with an alkali metal:

  (5)

Wherein z1 and z2 each represent a number that satisfies the conditions represented by the following equations, and p represents 0 or a positive number: $0 \leq z2/z1 < 10$, and $2 \leq (z1+z2) \leq 20$.

In addition, as an Al—Li hydrotalcite, a compound represented by the following Formula (6) can be used as well:

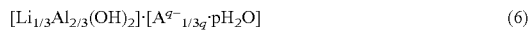  (6)

wherein $A^{q-}$ represents an anion having a valence of q; and p represents 0 or a positive number. Further, the carbonate anions in these hydrotalcites may be partially substituted with other anions.

These hydrotalcites may be dehydrated crystal water or may be those coated with, for example, a higher fatty acid such as stearic acid, a higher fatty acid metal salt such as alkali metal oleate, a metal organic sulfonate such as alkali metal dodecylbenzenesulfonate, a higher fatty acid amide, a higher fatty acid ester, or a wax.

The hydrotalcite may be a naturally-occurring or synthetic hydrotalcite. Examples of a hydrotalcite synthesis method include known methods that are described in JPS46-2280B1, JPS50-30039B1, JPS51-29129B1, JPH3-36839B1, JPS61-1741270A, JPH05-179052A; and the like. Further, the above-exemplified hydrotalcites can be used without any restriction in terms of their crystal structure, crystal particles and the like. These hydrotalcites may be used individually, or two or more thereof may be used in combination. In cases where the nucleating agent composition of the present invention contains a hydrotalcite, the content of the hydrotalcite may be adjusted such that it is 0.001 to 5 parts by mass with respect to 100 parts by mass of a polyolefin resin when the nucleating agent composition of the present invention is incorporated into the polyolefin resin.

Examples of the above-described antistatic agent include low-molecular-weight antistatic agents based on nonionic, anionic, cationic or amphoteric surfactants, and high-molecular-weight antistatic agents based on polymer compounds. Examples of the nonionic surfactants include polyethylene glycol-type nonionic surfactants, such as higher alcohol ethylene oxide adducts, fatty acid ethylene oxide adducts, higher alkylamine ethylene oxide adducts and polyolefin glycol ethylene oxide adducts; and polyhydric alcohol-type nonionic surfactants, such as polyethylene oxides, glycerin fatty acid esters, pentaerythritol fatty acid esters, sorbitol or sorbitan fatty acid esters, polyhydric alcohol alkyl ethers and alkanolamine aliphatic amides, Examples of the anionic surfactants include carboxylates, such as alkali metal salts of higher fatty acids; sulfates, such as higher alcohol sulfates and higher alkyl ether sulfates; sulfonates, such as alkylbenzenesulfonates, alkyl sulfonates and paraffin sulfonates; and phosphates such as higher alcohol phosphates. Examples of the cationic surfactants include quaternary ammonium salts such as alkyltrimethyl ammonium salts, and examples of the amphoteric surfactants include amino acid-type amphoteric surfactants such as higher alkylaminopropionates, and betaine-type amphoteric surfactants, such as higher alkyl dimethylbetaines and higher alkyl dihydroxyethylbetaines. In the polyolefin resin composition, an anionic surfactant is preferred, and a sulfonate such as an alkylbenzenesulfonate, an alkylsulfonate, or a paraffin sulfonate is particularly preferred. These antistatic agents may be used individually, or two or more thereof may be used in combination. In cases where the nucleating agent composition of the present invention contains a low-molecular-weight antistatic agent, the content of the low-molecular-weight antistatic agent may be adjusted such that it is 0.1 to 10 parts by mass with respect to 100 parts by mass of a polyolefin resin when the nucleating agent composition of the present invention is incorporated into the polyolefin resin.

Examples of the high-molecular-weight antistatic agents include ionomers, and block polymers containing a polyethylene glycol as a hydrophilic moiety. Examples of the ionomers include the ionomer disclosed in JP2010-132927A. Examples of the polymers containing a polyethylene glycol as a hydrophilic moiety include the polyether ester amide disclosed in JPH07-10989A, the polymer disclosed in U.S. Pat. No. 6,552,131B1 which is composed of a polyolefin and a polyethylene glycol, and the polymer disclosed in JP2016-023254A which is composed of a polyester and a polyethylene glycol. These high-molecular-weight antistatic agents may be used individually, or two or more thereof may be used in combination. In cases where the nucleating agent composition of the present invention contains a high-molecular-weight antistatic agent, the content of the high-molecular-weight antistatic agent may be adjusted such that it is 3 to 60 parts by mass with respect to 100 parts by mass of a polyolefin resin when the nucleating agent composition of the present invention is incorporated into the polyolefin resin.

The fluorescent brightener is a compound which enhances the whiteness or blueness of a molded article by a fluorescent action of absorbing ultraviolet rays of solar light and artificial light, converting the absorbed ultraviolet rays into visible light of purple to blue and radiating the visible light. Examples of the fluorescent brightener include C.I. Fluorescent Brightener 184, which is a benzoxazole-based compound; C.I. Fluorescent Brightener 52, which is a coumarin-based compound; and C.I. Fluorescent Brighteners 24, 85 and 71, which are diaminostyrylbenzyl sulfone-based compounds. These fluorescent brighteners may be used individually, or two or more thereof may be used in combination. In cases where the nucleating agent composition of the present invention contains a fluorescent brightener, the content of the fluorescent brightener may be adjusted such that it is 0.00001 to 0.1 parts by mass with respect to 100 parts by mass of a polyolefin resin when the nucleating agent composition of the present invention is incorporated into the polyolefin resin.

The pigment is not particularly restricted, and any commercially available pigment may be used. Specific examples of the pigment include PIGMENT RED 1, 2, 3, 9, 10, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; PIGMENT ORANGE 13, 31, 34, 36, 38, 43, 46, 48, 49, 51, 52, 55, 59, 60, 61, 62, 64, 65, and 71;

PIGMENT YELLOW 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; PIGMENT GREEN 7, 10, and 36; PIGMENT BLUE 15, 15:1, 15:2, 15:3, 15:4, 15:5, 15:6, 22, 24, 29, 56, 60, 61, 62, and 64; and PIGMENT VIOLET 1, 15, 19, 23, 27, 29, 30, 32, 37, 40, and 50.

Examples of the dye include azo dyes, anthraquinone dyes, indigoid dyes, triarylmethane dyes, xanthene dyes, alizarin dyes, acridine dyes, stilbene dyes, thiazole dyes, naphthol dyes, quinoline dyes, nitro dyes, indamine dyes, oxazine dyes, phthalocyanine dyes and cyanine dyes, and these dyes may be used individually, or two or more thereof may be used in combination.

A method of producing the nucleating agent composition of the present invention is not particularly restricted and, for example, a method of mixing the nucleating agent of the present invention with other additives may be employed. Examples of other method of producing the nucleating agent composition of the present invention include a method of mixing with heating the nucleating agent of the present invention and other additives along with a binder containing a polymer compound or a petroleum resin, homogenizing the resulting mixture in the presence of the binder in a molten state, and subsequently processing the resultant into a pellet form, According to this production method, the nucleating agent composition of the present invention that is uniform and has excellent ease of handling can be produced. In this production method, there is no restriction on the processing conditions. Further, the processing equipment to be used in this production method is also not restricted at all, and any well-known and commonly-used processing equipment, such as an extruder or a disk pelleter, may be employed.

<Polyolefin Resin Composition>

Next, the polyolefin resin composition of the present invention will be described. The resin composition of the present invention contains a polyolefin resin and a compound represented by Formula (1), and the content of the nucleating agent of the present invention is 0.001 to 10 parts by mass with respect to 100 parts by mass of the polyolefin resin. The resin composition of the present invention can allow its polyolefin resin to preferentially form β crystals.

Examples of the polyolefin resin contained in the resin composition of the present invention include α-olefin polymers, such as low-density polyethylenes (LUPE), linear low-density polyethylenes (L-LDPE), high-density polyethylenes (HDPE), isotactic polypropylenes, syndiotactic polypropylenes, hemi-isotactic polypropylenes, cycloolefin polymers, stereo block polypropylenes, poly-3-methyl-1-butenes, poly-3-methyl-1-pentenes, and poly-4-methyl-1-pentenes; α-olefin copolymers, such as ethylene-propylene copolymers, impact copolymer polypropylenes, ethylene-methyl methacrylate copolymers, ethylene-methyl acrylate copolymers, ethylene-ethyl acrylate copolymers, ethylene-butyl acrylate copolymers, ethylene-vinyl acetate copolymers, and ethylene-vinyl alcohol resins (EVOH); and chlorinated products thereof. The polyolefin resin may be a blend or an alloy of two or more of these polymers.

The polyolefin resin is preferably a polypropylene resin. Examples of the polypropylene resin include propylene homopolymers, ethylene-propylene copolymers (e.g., ethylene-propylene random copolymers), ethylene-propylene-1-butene terpolymers, copolymers of propylene and other α-olefin (e.g., 1-butene, 1-hexene, 1-octene, or 4-methyl-1-pentene), ethylene-propylene block copolymers containing an ethylene-propylene copolymer (e.g., impact copolymer polypropylenes and TPOs), and chlorinated products thereof. The polypropylene resin may be a blend, an alloy, or a block copolymer of two or more of these polymers.

It is more preferred that the polyolefin resin used in the resin composition of the present invention further contain an ethylene-propylene copolymer. In this case, the resulting molded article can be imparted with particularly excellent impact resistance. Examples of such a polyolefin resin include the above-described ethylene-propylene copolymers (e.g., ethylene-propylene random copolymers) and ethylene-propylene block copolymers (e.g., impact copolymer polypropylenes and TPOs).

In the resin composition of the present invention, the above-described polyolefin resins can be used regardless of, for example, the types and the presence or absence of a polymerization catalyst and a co-catalyst, the steric regularity, the average molecular weight, the molecular weight distribution, the presence or absence and the ratio of a component having a specific molecular weight, the specific gravity, the viscosity, the solubility in various solvents, the elongation rate, the impact strength, the crystallization degree, the X-ray diffraction, and the presence or absence of a modification/crosslinking treatment that is performed with an unsaturated carboxylic acid (e.g., maleic acid, itaconic acid, or fumaric acid) and a derivative thereof (e.g., maleic anhydride, maleic acid monoester, or maleic acid diester) or an organic peroxide, or by irradiation of an energy ray, or a combination of these treatments.

As described above, in the resin composition of the present invention, the content of the nucleating agent of the present invention is 0.001 to 10 parts by mass with respect to 100 parts by mass of the polyolefin resin. From the standpoint of attaining a superior β crystal-forming effect, the content of the nucleating agent of the present invention is preferably not less than 0.005 parts by mass, more preferably not less than 0.02 parts by mass, with respect to 100 parts by mass of the polyolefin resin. Further, from the standpoint of suppressing the occurrence of blooming and the extractability of the nucleating agent, the content of the nucleating agent of the present invention is preferably 1 part by mass or less, more preferably 0.5 parts by mass or less, still more preferably 0.3 parts by mass or less, with respect to 100 parts by mass of the polyolefin resin.

The resin composition of the present invention preferably further contains an elastomer. In this case, the resulting molded article can be imparted with a superior impact resistance.

The elastomer is not particularly restricted: however, it is preferably a copolymer of ethylene and a monomer other than ethylene since such an elastomer has excellent compatibility with polyolefin resins.

The monomer other than ethylene may be, for example, a linear or branched α-olefin having 3 to 20 carbon atoms, an aromatic vinyl compound having 8 to 20 carbon atoms, other vinyl compound, a conjugated diene, a (meth)acrylic acid alkyl ester, or an alkoxy-acrylic acid alkyl ester. It is noted here that "(meth)acrylic acid alkyl ester" refers to an acrylic acid alkyl ester or a methacrylic acid alkyl ester. These monomers other than ethylene may be used individually, or two or more thereof may be used in combination.

Examples of the α-olefin having 3 to 20 carbon atom include propylene, 1-butene, 3-methyl-1-butene, 3-ethyl-1-butene, 1-pentene, 3-methyl-1-pentene, 3-ethyl-1-pentene, 4,4-dimethyl-1-pentene, 1-hexene, 4-methyl-1-hexene, 4,4-dimethyl-1-hexene, 4-ethyl-1-hexene, 3-ethyl-1-hexene, 1-octene, 1-decease, 1-undecene, 1-dodecene, 1-tetradecene, 1-hexadecene, 1-octadecene and 1-eicosene, and the α-olefin is preferably, for example, propylene, 1-butene, 1-pentene, 1-hexene, or 1-octene.

Examples of the aromatic vinyl compound having 8 to 20 carbon atoms include styrene, o-methylstyrene, p-methylstyrene, m-methylstyrene, o-ethylstyrene, m-ethylstyrene, p-ethylstyrene, p-tert-butylstyrene, chloromethyl styrene and vinyltoluene, and the aromatic vinyl compound is preferably, for example, a mono- or poly-alkylstyrene.

Examples of the other vinyl compound include halogenated olefins, unsaturated amines, unsaturated carboxylic acids, vinyl esters, unsaturated epoxy compounds, and ethylenically unsaturated silane compounds.

The "halogenated olefins" refers to the above-described α-olefins to which a halogen atom, such as chlorine, bromine or iodine, is added.

Examples of the unsaturated amines include allylamine, 5-hexeneamine, and 6-hepteneamine.

Examples of the unsaturated carboxylic acids include (meth)acrylic acid, 3-butenoic acid, 4-pentenoic acid, 5-hexenoic acid, 6-heptenoic acid, 7-octenoic acid, 8-nonenoic acid, 9-decenoic acid and 10-undecenoic acid, and these unsaturated carboxylic acids may be substituted with a halogen atom.

Examples of the vinyl esters include aliphatic vinyl esters, such as vinyl formate, vinyl acetate, vinyl propionate, vinyl butyrate, vinyl isobutyrate, trimethyl vinyl acetate, vinyl pentanoate, vinyl decanoate, vinyl undecylate, vinyl laurate, vinyl myristate, vinyl pentadecylate, vinyl palmitate, vinyl stearate, and vinyl versatate (a mixture of carboxylic acids having 9 to 11 carbon atoms); and aromatic vinyl esters such as vinyl benzoate. Preferred examples of the vinyl esters include vinyl esters having 3 to 20 carbon atoms, and the vinyl esters may be, for example, more preferably vinyl esters having 4 to 10 carbon atoms, still more preferably vinyl acetate.

Examples of the unsaturated epoxy compounds include 4-epoxy-1-butene, 5-epoxy-1-pentene, 6-epoxy-1-hexene, 7-epoxy-1-heptene, 8-epoxy-1-octene, 9-epoxy-1-nonene, 10-epoxy-1-decene, and 11-epoxy-1-undecene.

Examples of the ethylenically unsaturated silane compounds include vinyl triethoxysilane, vinyl trimethoxysilane, 3-acryloxypropyltrimethoxysilane, and γ-methacryloxypropyltrimethoxysilane.

Examples of the conjugated diene include 1,3-butadiene, isoprene, 1,3-pentadiene, 2-ethyl-1,3-butadiene, 2,3-dimethylbutadiene, 2-methylpentadiene, 4-methylpentadiene, 2,4-hexadiene, and 1,3-octadiene.

Examples of the (meth)acrylic acid alkyl ester include methyl (meth)acrylate, ethyl (meth)acrylate, n-propyl (meth)acrylate, n-butyl (meth)acrylate, isobutyl (meth)acrylate, n-pentyl (meth)acrylate, isoamyl (meth)acrylate, n-hexyl (meth)acrylate, 2-methylpentyl (meth)acrylate, n-octyl (meth)acrylate, 2-ethylhexyl (meth)acrylate, n-decyl (meth)acrylate, n-dodecyl (meth)acrylate, and n-octadecyl (meth)acrylate.

Examples of the alkoxy-acrylic acid alkyl ester include 2-methoxyethyl acrylate, 2-ethoxyethyl acrylate, 2-(n-propoxy)ethyl acrylate, 2-(n-butoxy)ethyl acrylate, 3-methoxypropyl acrylate, 3-ethoxypropyl acrylate, 2-(n-propoxy)propyl acrylate, and 2-(n-butoxy)propyl acrylate.

The elastomer may be a copolymer of any one of these monomers with ethylene, or a copolymer of a combination of two or more of these monomers with ethylene.

Among elastomers that are copolymers of ethylene and a monomer other than ethylene, an ethylene-α olefin copolymer is preferred since it has excellent compatibility with olefin resins. Further, a copolymer of ethylene and vinyl ester is also preferred.

Specific examples of an elastomer that is a copolymer of ethylene and a monomer other than ethylene include ethylene-propylene copolymers, ethylene-butene copolymers, block or random copolymers such as ethylene-octene copolymers, ethylene-methyl methacrylate copolymers, ethylene-methyl acrylate copolymers, ethylene-ethyl acrylate copolymers, ethylene-butyl acrylate copolymers, styrene-ethylene-butylene copolymers, styrene-ethylene-butylene-styrene copolymers, and ethylene-vinyl acetate copolymers.

Examples of an elastomer other than the elastomer that is a copolymer of ethylene and a monomer other than ethylene include thermoplastic polyesters and thermoplastic polyurethanes.

The above-described elastomers can be used regardless of, for example, the molecular weight, the polymerization degree, the density, the softening point, the insoluble component-to-solvent ratio, the degree of stereoregularity, the presence or absence of a catalyst residue, the type and blend ratio of a raw material monomer, and the type of a polymerization catalyst (e.g., a Ziegler catalyst or a metallocene catalyst).

The content of the elastomer is preferably 1 to 80 parts by mass with respect to 100 parts by mass of the polyolefin resin. In this case, the resin composition of the present invention can impart its molded article with superior impact resistance. The content of the elastomer is more preferably not less than 3 parts by mass, particularly preferably not less than 5 parts by mass, with respect to 100 parts by mass of the polyolefin resin. Further, from the standpoint of obtaining a molded article that has excellent impact resistance in low-temperature environments, the content of the elastomer is more preferably 50 parts by mass or less, particularly preferably 40 parts by mass or less, with respect to 100 parts by mass of the polyolefin resin.

The resin composition of the present invention preferably further contains a filler. In this case, the resulting molded article can be imparted with excellent rigidity. Examples of the filler include the same ones as those that can be used in the above-described nucleating agent composition. Among such fillers, talc is particularly preferred since it can impart the molded article with especially excellent rigidity and is easy to obtain. The content of the filler is preferably 0.01 to 80 parts by mass with respect to 100 parts by mass of the polyolefin resin. The content of the filler is more preferably not less than 1 part by mass with respect to 100 parts by mass of the polyolefin resin. Further, the content of the filler is more preferably 50 parts by mass or less with respect to 100 parts by mass of the polyolefin resin.

In the polyolefin resin composition, unless the performance thereof is not greatly deteriorated, an additive(s) generally used in polyolefin resins, such as a phenolic antioxidant, a phosphorus-based antioxidant, a sulfur-based antioxidant, other antioxidant, a hindered amine compound, an ultraviolet absorber, other nucleating agent different from the compound represented by Formula (1), a flame retardant, a flame retardant aid, a lubricant, a hydrotalcite, a fatty acid metal salt, an antistatic agent, a fluorescent brightener, a pigment and a dye, may further be incorporated. Examples of these additives include the same ones as those that can be used in the above-described nucleating agent composition. The amounts of these additives to be incorporated are not particularly restricted, and these additives may be incorporated such that they each exist at an appropriate concentration in the polyolefin resin.

A method of producing the resin composition of the present invention is not particularly restricted, and examples thereof include a method of dry-blending the polyolefin resin in a powder or pellet form with the nucleating agent of the present invention and other additives; a method of melt-kneading a mixture obtained by dry-blending the polyolefin resin in a powder or pellet form with the nucleating agent of the present invention and other additives; and a method of processing the nucleating agent of the present invention and other additives into a pellet form and subsequently adding the pellet to the polyolefin resin. The nucleating agent of the present invention and other additives may be added to the polyolefin resin simultaneously or separately. Further, the method of producing the resin composition of the present invention may be a method of incorporating the nucleating agent composition of the present invention into the polyolefin resin.

<Polyolefin Resin Masterbatch>

Examples of other method of producing the resin composition of the present invention include a method of preparing the masterbatch of the present invention and incorporating this masterbatch into the polyolefin resin. The masterbatch of the present invention contains a polyolefin resin and the above-described nucleating agent of the present invention. The masterbatch of the present invention can allow its polyolefin resin to preferentially form β crystals. The masterbatch of the present invention may further contain other additives as required. The polyolefin resin contained in the masterbatch of the present invention is not particularly restricted, and examples thereof include the above-exemplified polyolefin resins. A method of producing the masterbatch of the present invention is not particularly restricted, and examples thereof include a method of melt-kneading a mixture obtained by dry-blending the polyolefin resin in a powder or pellet form with the nucleating agent of the present invention and other additives.

<Molded Article>

Next, the molded article of the present invention will be described. The molded article of the present invention is composed of the resin composition of the present invention. The resin composition of the present invention can allow its polyolefin resin to preferentially form β crystals; therefore, the molded article of the present invention contains β crystals of the polyolefin resin.

Examples of the molded article of the present invention include injection-molded articles, fibers, flat yarns, biaxially stretched films, uniaxially stretched films, unstretched films, sheets, thermoformed articles, extrusion blow-molded articles, injection blow-molded articles, injection stretch blow-molded articles, profile extrusion-molded articles, and rotary molded articles. More specific examples of the molded article of the present invention include automotive exterior components, automotive interior components, housings, containers, and pipes.

A method of molding the molded article of the present invention is not particularly restricted and examples thereof include injection molding, extrusion molding, blow molding, rotational molding, vacuum molding, inflation molding, calender molding, slush molding, dip molding, and thermoform molding.

Next, the automotive exterior component, automotive interior component, housing, container, and pipe according to the present invention will be described.

<Automotive Exterior Component>

The resin composition of the present invention can allow its polyolefin resin to preferentially form β crystals; therefore, an automotive exterior component composed of the resin composition of the present invention has excellent impact resistance. Examples of the automotive exterior component include bumpers, radiator grilles, front grilles, front panels, fenders, pillars, pillar covers, door mirror stay covers, glass run channels, door mirror housings, lamp housings, wheel covers, spoilers, air spoilers, weather-strips, window moldings, belt moldings, sunroofs, front-end modules, door modules, back door modules, and outer plates. Examples of a method of molding the automotive exterior component include injection molding, thermoform molding, and blow molding.

<Automotive interior Component>

The resin composition of the present invention can allow its polyolefin resin to preferentially form β crystals; therefore, an automotive interior component composed of the resin composition of the present invention has excellent impact resistance. Examples of the automotive interior component include instrument panels, door trim panels, pillar trims, door trims, pillar garnishes, package trays, rear trays, console boxes, and air-conditioning ducts. Examples of a method of molding the automotive interior component include injection molding, thermoform molding, and blow molding.

<Housing>

The resin composition of the present invention can allow its polyolefin resin to preferentially form β crystals; therefore, a housing composed of the resin composition of the present invention has excellent impact resistance. Examples of the housing include housings for home electric appliances, housings for arcade gaming machines, housings for home-use gaming machines, housing s for portable gaming machines, housings for cameras, housings for cellular phones, housings for smartphones, housings for electronic devices, housings for secondary batteries, and housings for safety breakers. Examples of a method of molding the housing include injection molding, thermoform molding, and blow molding.

<Container>

The resin composition of the present invention can allow its polyolefin resin to preferentially form β crystals; therefore, a container composed of the resin composition of the present invention has excellent impact resistance. Examples of the container include tableware; food containers, such as precooked food containers, frozen food containers, microwavable heat-resistant containers, frozen storage containers, retort containers, cups, and frozen dessert cups; bottle containers, such as beverage bottles, infusion bottles, and medical hollow bottles; containers for physicochemical tests, such as beakers and graduated cylinders; chemical containers; medical containers; detergent containers; cosmetic containers; perfume containers; and toner containers. Examples of a method of molding the container include blow molding, inflation molding, and thermoform molding.

<Pipe>

The resin composition of the present invention can allow its polyolefin resin to preferentially form β crystals; therefore, a pipe composed of the resin composition of the present invention has excellent impact resistance. Examples of the pipe include various pipes, such as infrastructure pipes (e.g., water pipes and gas pipes), plant utility pipes, vehicle fuel delivery pipes, and vehicle air intake pipes; various tubes, such as cosmetic/perfume spray tubes, medical tubes, and infusion tubes; various hoses, such as water hoses and vehicle air duct hoses. Examples of a method of molding the pipe include injection molding, extrusion molding, and rotomolding.

<Film>

Next, a film will be described. The film of the present invention is composed of the resin composition of the present invention. The resin composition of the present invention can allow its polyolefin resin to preferentially form β crystals; therefore, the film of the present invention has excellent stretchability. In addition, since the β crystals of the polyolefin resin have a lower melting point than α crystals, the film of the present invention has excellent heat sealing properties. Examples of a method of molding the film include extrusion molding, inflation molding, and cast molding.

<Porous Film>

Heating causes β crystals of a polyolefin resin to undergo a phase transition into α crystals. In addition, β crystals of a polyolefin resin have a lower density than α crystals. Therefore, the porous film of the present invention can be produced by a production method that includes: the molding step of molding the resin composition of the present invention to obtain a film; and the step of heat-stretching the film obtained by the molding step, and the porous film of the present invention contains fine and uniform voids. The porous film of the present invention can be suitably used as, for example, a light reflection film or a battery separator. The temperature at which the film is heat-stretched is not particularly restricted, and it may be, for example, 80 to 120° C. The stretching may be performed uniaxially or biaxially. The stretching ratio is also not particularly restricted and may be, for example, 1.1 to 10.

<Light Reflection Film>

The porous film of the present invention contains fine and uniform voids; therefore, the light reflection film of the present invention that is composed of the film of the present invention exhibits excellent light reflection. The light reflection film of the present invention can be suitably used as, for example, a plate material integrated into a backlight of a liquid crystal display, specifically an edge light reflector, a direct-type backlight reflector, or a reflector around a cold-cathode tube, for a liquid crystal display.

<Battery Separator>

The porous film of the present invention contains fine and uniform voids; therefore, the battery separator of the present invention that is composed of the porous film of the present invention has excellent transparency. Such a battery separator can be suitably used in, for example, lithium secondary batteries, nickel-hydrogen batteries, nickel-cadmium batteries, and polymer batteries.

<Package>

Next, the package of the present invention will be described. The package of the present invention includes the film of the present invention. The film of the present invention has excellent heat sealing properties; therefore, the package of the present invention also has excellent heat sealing properties. The package of the present invention may consist of only the film of the present invention, or may be composed of a laminate in which the film of the present invention is laminated on a substrate. In the laminate, the film of the present invention may be laminated on the substrate via an intermediate layer made of a polyolefin film or the like. Examples of the substrate constituting the laminate include films of a polyolefin resin, a styrene resin, a polyester, or a polyamide; stretched films thereof; laminated films constituted by any of these films and a resin film having gas barrier properties, such as a polyamide film or an ethylene-vinyl alcohol copolymer film; metal foils such as an aluminum foil; and vapor-deposited films and papers; on which aluminum, silica or the like is vapor-deposited.

Examples of a method of producing the laminate include dry lamination and coextrusion. The package of the present invention can be suitably used for packaging food products, electronic materials and the like, particularly for retort packaging and packaging using an automatic packaging machine.

EXAMPLES

The present invention will now be described more concretely by way of Examples thereof; however, the present invention is not restricted by the following Examples and the like by any means.

Examples 1-1 to 1-10 and Comparative Examples 1-1 to 1-4

To 200 g of a homopolypropylene (MFR at 230° C., under a load of 2.16 kg=8 g/10 min), 0.05% by mass of a phenolic antioxidant (tetrakis[methylene-3-(3',5'-di-tert-butyl-4'-hydroxyphenyl)propionate]methane), 0.1% by mass of a phosphorus-based antioxidant (tris(2,4-di-tert-butylphenyl)phosphite), 0.05% by mass of calcium stearate, and 0.1% by mass of the respective nucleating agents for polyolefin resin shown in Table 1 were added and manually blended for 3 minutes, and the resultants were each subsequently loaded to a uniaxial extruder (apparatus: LABO-PLASTOMILL μ, manufactured by Toyo Seiki Seisaku-sho, Ltd.) and granulated at a melt temperature of 230° C. It is noted here that in Comparative Example 1-1, granulation was performed in the same procedures as in Example 1-1, except that no nucleating agent for polyolefin resin was added. The thus granulated pellets were dried at 80° C. for 8 hours and then evaluated under the below-described conditions. In Table 1, the "steric structure" of each nucleating agent for polyolefin resin represents the steric structure of an aspartic acid residue, and Z represents one of the following groups.

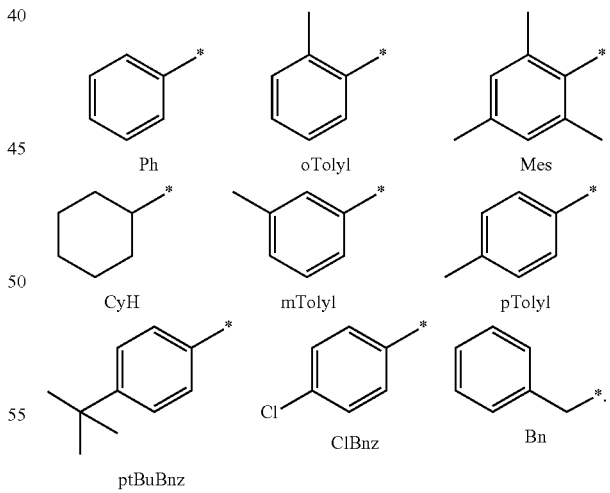

<Crystallization Temperature Tc [° C.]>

For the thus obtained pellets, the crystallization temperature (Tc) was measured using a differential scanning calorimeter (apparatus: DIAMOND, manufactured by PerkinElmer Co., Ltd.). Each pellet was heated from room temperature to 230° C. at a rate of 50° C./mini, maintained for 5 minutes and then cooled to 50° C. at a rate of 10° C./min, and the crystallization temperature was determined as the temperature (° C.) of an exothermic peak observed during the cooling process. The results thereof are shown in Table 1.

<β-Crystal Ratio>

For the thus obtained pellets, the presence or absence of β crystals was determined and the β-crystal ratio was measured using a differential scanning calorimeter (apparatus: DIAMOND, manufactured by PerkinElmer Co., Ltd.). Specifically, each pellet was heated from room temperature to 230° C. at a rate of 50° C./min, maintained for 20 minutes, cooled to 50° C. at a rate of 10° C./min, further maintained for 5 minutes and then heated again to 230° C. at a rate of 10° C./min and, in the second heating process, β crystals were judged to be "present" when both an endothermic peak having a peak top at about 150° C. and an endothermic peak having a peak top at about 165° C. were observed, while β crystals were judged to be "absent" when only an endothermic peak having a peak top at about 165° C. was observed. When β crystals were judged to be "present", the area of the endothermic peak having a peak top at about 150° C. and the area of the endothermic peak having a peak top at about 165° C. were defined as "β-crystal area" and "α-crystal area", respectively, and the β-crystal ratio was calculated by the following equation:

β-crystal ratio=β-crystal area/α-crystal area+β-crystal area)×100(%)

The results thereof are shown in Table 1.

<Coloration>

The thus obtained pellets were injection-molded at 200° C., and the presence or absence of coloration was visually determined for each of the resulting 1 mm-thick test pieces. The results thereof are shown in Table 1.

TABLE 1

|  | Nucleating agent for polyolefin resin | | | | | Tc (° C.) | Presence or absence of β crystals | β-crystal ratio(%) | Coloration |
| --- | --- | --- | --- | --- | --- | --- | --- | --- | --- |
|  | Z | M | x | a | b | Steric structure |  |  |  |
| Example 1-1 | Ph | Na | 1 | 2 | 1 | D | 127.4 | present | 80.1 | absent |
| Example 1-2 | Ph | Ca | 2 | 1 | 1 | D | 117.2 | present | 44.4 | absent |
| Example 1-3 | Ph | AlOH | 2 | 1 | 1 | D | 116.4 | present | 3.4 | absent |
| Example 1-4 | CyH | Na | 1 | 2 | 1 | D | 119.9 | present | 17.5 | absent |
| Example 1-5 | pH | Na | 1 | 2 | 1 | L | 126.3 | present | 79.6 | absent |
| Example 1-6 | CyH | Na | 1 | 2 | 1 | L | 124.0 | present | 54.8 | absent |
| Example 1-7 | Mes | Na | 1 | 2 | 1 | L | 116.9 | present | 35.2 | absent |
| Example 1-8 | mTolyl | Na | 1 | 2 | 1 | L | 117.0 | present | 22.1 | absent |
| Example 1-9 | pTolyl | Na | 1 | 2 | 1 | L | 122.0 | present | 28.3 | absent |
| Example 1-10 | ClBnz | Na | 1 | 2 | 1 | L | 118.8 | present | 51.3 | absent |
| Comparative Example 1-1 | — | — | — | — | — | — | 113.7 | absent | — | absent |
| Comparative Example 1-2 | pH | Zn | 2 | 1 | 1 | D | 115.9 | absent | — | absent |
| Comparative Example 1-3 | CyH | Zn | 2 | 1 | 1 | D | 122.7 | absent | — | absent |
| Comparative Example 1-4 | CyH | Zn | 2 | 1 | 1 | L | 123.0 | absent | — | absent |

Examples 2-1 to 2-10 and Comparative Examples 2-1 to 2-5

To 200 g of a homopolypropylene (MFR at 230° C. under a load of 2.16 kg=8 g/10 min), 0.05% by mass of a phenolic antioxidant (tetrakis[methylene-3-(3',5'-di-tert-butyl-4'-hydroxyphenyl)propionate]methane), 0.1% by mass of a phosphorus-based antioxidant (tris(2,4-di-tert-butylphenyl)phosphite), 0.05% by mass of calcium stearate, and 0.1% by mass of the respective compounds shown in Table 2 were added and manually blended for 3 minutes, and the resultants were each subsequently loaded to a uniaxial extruder (apparatus: LABO-PLASTOMILL μ, manufactured by Thyo Seiki Seisaku-sho, Ltd) and granulated at a melt temperature of 230° C., In Table 2, the "steric structure" of each nucleating agent for polyolefin resin represents the steric structure of an aspartic acid residue, and Z represents one of the above-described groups.

The thus granulated pellets were dried at 80° C. for 8 hours, after which the crystallization temperature [° C.], the β-crystal ratio, and the presence or absence of coloration were evaluated by the same procedures as in Example 1-1. The results thereof are shown in Table 2.

TABLE 2

| | Nucleating agent for polyolefin resin | | | | | | Presence or | | |
| | Z | M | x | a | b | Steric structure | Tc (° C.) | absence of β crystals | β-crystal ratio(%) | Coloration |
|---|---|---|---|---|---|---|---|---|---|---|
| Example 2-1 | Ph | Ca | 2 | 1 | 1 | racemic body | 127.4 | present | 1.8 | absent |
| Example 2-2 | Bn | Ca | 2 | 1 | 1 | racemic body | 116.6 | present | 19.7 | absent |
| Example 2-3 | Mes | Na | 1 | 2 | 1 | racemic body | 118.4 | present | 54.4 | absent |
| Example 2.-4 | Mes | Ca | 2 | 1 | 1 | racemic body | 116.8 | present | 12.7 | absent |
| Example 2-5 | Mes | AlOH | 2 | 1 | 1 | racemic body | 125.6 | present | 77.3 | absent |
| Example 2-6 | pTolyl | Na | 1 | 2 | 1 | racemic body | 120.6 | present | 64.3 | absent |
| Example 2-7 | ptBuBnz | Na | 1 | 2 | 1 | racemic body | 117.0 | present | 59.8 | absent |
| Example 2-8 | ptBuBnz | Ca | 2 | 1 | 1 | racemic body | 117.3 | present | 2.9 | absent |
| Example 2-9 | ptBuBnz | AlOH | 2 | 1 | 1 | racemic body | 117.4 | present | 1.1 | absent |
| Example 2-10 | ClBnz | Na | 1 | 2 | 1 | racemic body | 118.5 | present | 28.1 | absent |
| Comparative Example 2-1 | CyH | Zn | 2 | 1 | 1 | racemic body | 126.5 | absent | — | absent |
| Comparative Example 2-2 | Mes | Zn | 2 | 1 | 1 | racemic body | 116.7 | absent | — | absent |
| Comparative Example 2-3 | ptBuBnz | Zn | 2 | 1 | 1 | racemic body | 117.0 | absent | — | absent |
| Comparative Example 2-4 | pTolyl | Zn | 2 | 1 | 1 | racemic body | 118.1 | absent | — | absent |
| Comparative Example 2-5 | quinacridone | | | | | | — | —* | —* | present |

*The Tc and the presence or absence of β- crystals were not evaluated due to severe coloration of quinacridone.

Comparative Examples 3-1 to 3-6

To 200 g of a homopolypropylene (MFR at 230° C. under a load of 2.16 kg=8 g/10 min), 0.05% by mass of a phenolic antioxidant (tetrakis-[methylene-3-(3',5'-di-tert-butyl-4'-hydroxyphenyl)propionate]methane), 0.1% by mass of a phosphorus-based antioxidant (tris(2,4-di-tert-butylphenyl)phosphite), 0.05% by mass of calcium stearate, and 0.1% by mass of the respective comparative compounds represented by Formula (7) wherein Z was as shown in Table 3 were added and manually blended for 3 minutes, and the resultants were each subsequently loaded to a uniaxial extruder (apparatus: LABO-PLASTOMILL μ, manufactured by Toyo Seiki Seisaku-sho, Ltd.) and granulated at a melt temperature of 230° C. In Table 3 and Formula (7), Z represents one of the above-described groups. The thus granulated pellets were dried at 80° C. for 8 hours, after which the crystallization temperature Tc [° C.] and the β-crystal ratio were evaluated by the same procedures as in Example 1-1. The results thereof are shown in Table 3.

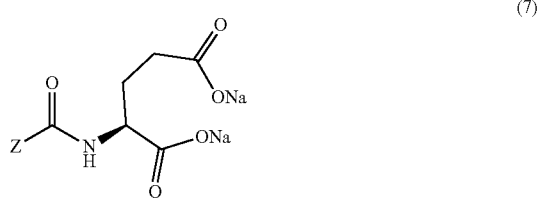

(7)

TABLE 3

| | Comparative compound Z | Tc (° C.) | Presence or absence of β crystals | β-crystal ratio (%) |
|---|---|---|---|---|
| Comparative Example 3-1 | Ph | 117.9 | absent | — |
| Comparative Example 3-2 | CyH | 119.1 | absent | — |
| Comparative Example 3-3 | pTolyl | 115.3 | absent | — |
| Comparative Example 3-4 | mTolyl | 115.0 | absent | — |
| Comparative Example 3-5 | oTolyl | 115.2 | absent | — |
| Comparative Example 3-6 | Mes | 116.0 | absent | — |

Examples 4-1 to 4-9 and Comparative Examples 4-1 to 4-41

A resin mixture was prepared by blending 70 parts by mass of an impact copolymer polypropylene (PRIME POLYPRO J707G, manufactured by Prime Polymer Co., Ltd.), 10 parts by mass of an ethylene-octene copolymer elastomer (ENGAGE 8842, manufactured by The Dow Chemical Company), and 20 parts by mass of talc (water content=0.1% by mass, particle size $D_{50}$ determined by laser diffractometry=14.0 μm, bulk specific gravity determined by the measurement method prescribed in JIS K5101=0.32 g/mL), To 2 kg of this resin mixture, 0.05% by mass of a phenolic antioxidant (tetrakis[methylene-3-(3',5'-tert-butyl-4'-hydroxyphenyl)propionate]methane), 0.1% by mass of a phosphorus-based antioxidant (tris(2,4-di-tert-butylphenyl) phosphite), 0.05% by mass of calcium stearate, and each nucleating agent for polyolefin resin shown in Table 4 or 5 in the shown in Table 4 or 5 were added and blended for 30 minutes using a rocking mixer (manufactured by Aichi Electric Co., Ltd.), after which resultants were each loaded to a biaxial extruder (TEX-25αIII, manufactured by The Japan Steel Works, Ltd.) and granulated at a melt temperature of 230° C. It is noted here that in Comparative Example 4-1, granulation was performed in the same procedures as in Example 4-1, except that no nucleating agent for polyolefin resin was added. In Tables 4 and 5, the "steric structure" of each nucleating agent for polyolefin resin represents the steric structure of an aspartic acid residue, and Z represents one of the above-described groups.

content=(11% by mass, particle size $D_{50}$ determined by laser diffractometry=14.0 um, bulk specific gravity determined by a measurement method prescribed in JIS K5101=0.32 g/mL). To 2 kg of this resin mixture, 0.05% by mass of a phenolic antioxidant (tetrakis[methylene-3-(3',5'-tert-butyl-4'-hydroxyphenyl)propionate]methane), 0.1% by mass of a phosphorus-based antioxidant (tris(2,4-di-tart-butylphenyl) phosphite), 0.05% by mass of calcium stearate, and each nucleating agent for polyolefin resin shown in Table 6 or 7 in the amount shown in Table 6 or 7 were added and blended for 30 minutes using a rocking mixer (manufactured by Aichi Electric Co., Ltd.), after which resultants were each loaded to a biaxial extruder (TEX-25αIII, manufactured by

TABLE 4

| | Nucleating agent for polyolefin resin | | | | | Added amount (% by mass) | Tc (° C.) | Presence or absence of β crystals | β-crystal ratio (%) |
|---|---|---|---|---|---|---|---|---|---|
| | Z | M | x | a | b | Steric structure | | | |
| Example 4-1 | Ph | Na | 1 | 2 | 1 | L | 0.02 | 129 | present | 51 |
| Example 4-2 | Ph | Na | 1 | 2 | 1 | L | 0.05 | 130 | present | 53 |
| Example 4-3 | Ph | Na | 1 | 2 | 1 | L | 0.1 | 130 | present | 53 |
| Example 4-4 | CyH | Na | 1 | 2 | 1 | L | 0.05 | 130 | present | 36 |
| Example 4-5 | ClBnZ | Na | 1 | 2 | 1 | L | 0.05 | 129 | present | 34 |
| Example 4-6 | Ph | Na | 1 | 2 | 1 | D | 0.05 | 130 | present | 52 |
| Example 4-7 | Ph | Ca | 2 | 1 | 1 | D | 0.05 | 129 | present | 30 |
| Example 4-8 | pTolyl | Na | 1 | 2 | 1 | racemic body | 0.05 | 129 | present | 43 |
| Example 4-9 | Mes | Al(OH) | 2 | 1 | 1 | racemic body | 0.05 | 130 | present | 51 |
| Comparative Example 4-1 | — | — | — | — | — | — | 0 | 129 | absent | — |
| Comparative Example 4-2 | Ph | Zn | 2 | 1 | 1 | D | 0.05 | 130 | absent | — |
| Comparative Example 4-3 | CyH | Zn | 2 | 1 | 1 | L | 0.05 | 130 | absent | — |
| Comparative Example 4-4 | CyH | Zn | 2 | 1 | 1 | racemic body | 0.05 | 130 | absent | — |

TABLE 5

| | Nucleating agent for polyolefin resin | | | | | Added amount (% by mass) | Charpy impact strength (kJ/m$^2$) |
|---|---|---|---|---|---|---|---|---|
| | Z | M | x | a | b | Steric structure | | |
| Example 4-2 | Ph | Na | 1 | 2 | 1 | L | 0.05 | 12 |
| Example 4-4 | CyH | Na | 1 | 2 | 1 | L | 0.05 | 10 |
| Example 4-6 | Ph | Na | 1 | 2 | 1 | D | 0.05 | 12 |
| Example 4-8 | pTolyl | Na | 1 | 2 | 1 | racemic body | 0.05 | 10 |
| Example 4-9 | Mes | Al(OH) | 2 | 1 | 1 | racemic body | 0.05 | 11 |
| Comparative Example 4-1 | — | — | — | — | — | — | 0 | 8 |
| Comparative Example 4-2 | Ph | Zn | 2 | 1 | 1 | D | 0.05 | 8 |

Examples 5-1 to 5-9 and Comparative Examples 5-1 to 5-4

A resin mixture was prepared by blending 60 parts by mass of an impact copolymer polypropylene (PRIME POLYPRO J707G, manufactured by Prime Polymer Co., Ltd.), 20 parts by mass of an ethylene-octene copolymer elastomer (ENGAGE 8842, manufactured by The Dow Chemical Company), and 20 parts by mass of talc (water The Japan Steel Works, Ltd.) and granulated at a melt temperature of 230° C. In Tables 6 and 7, the "steric structure" of each nucleating agent for polyolefin resin represents the steric structure of an aspartic acid residue, and Z represents one of the above-described groups. It is noted here that in Comparative Example 5-1, granulation was performed in the same procedures as in Example 5-1, except that no nucleating agent for polyolefin resin was added.

TABLE 6

| | Nucleating agent for polyolefin resin | | | | | | Added amount (% by mass) | Tc (° C.) | Presence or absence of β crystals | β-crystal ratio (%) |
|---|---|---|---|---|---|---|---|---|---|---|
| | Z | M | x | a | b | Steric structure | | | | |
| Example 5-1 | Ph | Na | 1 | 2 | 1 | L | 0.02 | 130 | present | 53 |
| Example 5-2 | Ph | Na | 1 | 2 | 1 | L | 0.05 | 131 | present | 54 |
| Example 5-3 | Ph | Na | 1 | 2 | 1 | L | 0.1 | 131 | present | 54 |
| Example 5-4 | CyH | Na | 1 | 2 | 1 | L | 0.05 | 130 | present | 35 |
| Example 5-5 | ClBnZ | Na | 1 | 2 | 1 | L | 0.05 | 130 | present | 33 |
| Example 5-6 | Ph | Na | 1 | 2 | 1 | D | 0.05 | 131 | present | 52 |
| Example 5-7 | Ph | Ca | 2 | 1 | 1 | D | 0.05 | 130 | present | 31 |
| Example 5-8 | pTolyl | Na | 1 | 2 | 1 | racemic body | 0.05 | 130 | present | 42 |
| Example 5-9 | Mes | Al(OH) | 2 | 1 | 1 | racemic body | 0.05 | 130 | present | 52 |
| Comparative Example 5-1 | — | — | — | — | — | — | 0 | 130 | absent | — |
| Comparative Example 5-2 | Ph | Zn | 2 | 1 | 1 | D | 0.05 | 129 | absent | — |
| Comparative Example 5-3 | CyH | Zn | 2 | 1 | 1 | L | 0.05 | 129 | absent | — |
| Comparative Example 5-4 | CyH | Zn | 2 | 1 | 1 | racemic body | 0.05 | 130 | absent | — |

TABLE 7

| | Nucleating agent for polyolefin resin | | | | | | Added amount (% by mass) | Charpy impact strength (kJ/m$^2$) |
|---|---|---|---|---|---|---|---|---|
| | Z | M | x | a | b | Steric structure | | |
| Example 5-2 | Ph | Na | 1 | 2 | 1 | L | 0.05 | 41 |
| Example 5-4 | CyH | Na | 1 | 2 | 1 | L | 0.05 | 37 |
| Example 5-6 | Ph | Na | 1 | 2 | 1 | D | 0.05 | 41 |
| Example 5-8 | pTolyl | Na | 1 | 2 | 1 | racemic body | 0.05 | 37 |
| Example 5-9 | Mes | Al(OH) | 2 | 1 | 1 | racemic body | 0.05 | 39 |
| Comparative Example 5-1 | — | — | — | — | — | — | 0 | 34 |
| Comparative Example 5-2 | Ph | Zn | 2 | 1 | 1 | D | 0.05 | 34 |

Examples 6-1 to 6-4 and Comparative Examples 6-1 and 6-2

To 2 kg of an impact copolymer polypropylene (PRIME POLYPRO J707G, manufactured by Prime Polymer Co., Ltd.), 0.05% by mass of a phenolic antioxidant (tetrakis [methylene-3',5'-di-tert-butyl-4'-hydroxyphenyl)propionate] methane), 0.1% by mass of a phosphorus-based antioxidant (tris(2,4-di-tert-butylphenyl)phosphite), 0.05% by mass of calcium stearate, and each nucleating agent for polyolefin resin shown in Table 8 in the amount shown in Table 8 were added and blended for 30 minutes using a rocking mixer (manufactured by Aichi Electric Co., Ltd.), after which resultants were each loaded to a biaxial extruder (TEX-25αIII, manufactured by The Japan Steel Works, Ltd.) and granulated at a melt temperature of 230° C. In Table 8, the "steric structure" of each nucleating agent for polyolefin resin represents the steric structure of an aspartic acid residue, and Z represents one of the above-described groups. It is noted here that in Comparative Example 6-1, granulation was performed in the same procedures as in Example 6-1, except that no nucleating agent for polyolefin resin was added.

TABLE 8

| | Nucleating agent for polyolefin resin | | | | | Steric structure | Added amount (% by mass) | Tc (° C.) | Presence or absence of β crystals | β-crystal ratio (%) | Charpy impact strength (kJ/m$^2$) |
|---|---|---|---|---|---|---|---|---|---|---|---|
| | Z | M | x | a | b | | | | | | |
| Example 6-1 | Ph | Na | 1 | 2 | 1 | L | 0.05 | 123 | present | 99 | 12 |
| Example 6-2 | CyH | Na | 1 | 2 | 1 | L | 0.05 | 118 | present | 85 | 10 |
| Example 6-3 | pTolyl | Na | 1 | 2 | 1 | racemic body | 0.05 | 119 | present | 87 | 10 |
| Example 6-4 | Mes | Al(OH) | 2 | 1 | 1 | racemic body | 0.05 | 122 | present | 99 | 12 |
| Comparative Example 6-1 | — | — | — | — | — | — | 0 | 114 | absent | — | 8 |

TABLE 8-continued

| | Nucleating agent for polyolefin resin | | | | Steric | Added amount | Tc | Presence or absence of | β-crystal | Charpy impact |
|---|---|---|---|---|---|---|---|---|---|---|
| | Z | M | x | a | b | structure | (% by mass) | (° C.) | β crystals | ratio (%) | strength (kJ/m²) |
| Comparative Example 6-2 | Ph | Zn | 2 | 1 | 1 | D | 0.05 | 122 | absent | — | 8 |

The polyolefin resin composition pellets of Examples 4-1 to 4-9, Comparative Examples 4-1 to 4-4, Examples 5-1 to 5-9, Comparative Examples 5-1 to 5-4, Examples 6-1 to 6-4 and Comparative Examples 6-1 and 6-2, which were granulated in the above-described manner, were dried at 80° C. for 8 hours. Using each of the thus dried polyolefin resin composition pellets, the crystallization temperature was evaluated was evaluated by the same procedures as in Example 1-1, and the β-crystal ratio and the Charpy impact strength were also evaluated by the below-described procedures. The results thereof are shown in Tables 4 to 8.

<β-Crystal Ratio>

For the thus obtained pellets, the presence or absence of β crystals was determined and the β-crystal ratio was measured using a differential scanning calorimeter (apparatus: DIAMOND, manufactured by PerkinElmer Co., Ltd.). Specifically, each pellet was heated from room temperature to 230° C. at a rate of 50° C./min, maintained for 20 minutes, cooled to 50° C. at a rate of 10° C./min, further maintained for 5 minutes and then heated again to 230° C. at a rate of 30° C./min and, in the second heating process, β crystals were judged to be "present" when both an endothermic peak having a peak top at about 150° C. and an endothermic peak having a peak top at about 165° C. were observed, while β crystals were judged to be "absent" when only an endothermic peak having a peak top at about 165° C. was observed. When β crystals were judged to be "present", the area of the endothermic peak having a peak top at about 150° C. and the area of the endothermic peak having a peak top at about 165° C. were defined as "β-crystal area" and "α-crystal area", respectively, and the β-crystal ratio was calculated by the following equation:

$$\beta\text{-crystal ratio} = \beta\text{-crystal area}/(\alpha\text{-crystal area} + \beta\text{-crystal area}) \times 100(\%)$$

<Charpy Impact Strength>

The pellets obtained above were each molded at a resin temperature of 231° C. and a mold temperature of 50° C. using an injection molding machine (apparatus: horizontal injection molding machine NEX80, manufactured by Nissei Plastic Industrial Co., Ltd.) to prepare test pieces for the measurement of Charpy impact strength (80 mm×10 mm×4 mm). The thus obtained test pieces were left to stand for 7 days in an incubator at a temperature of 23° C. and a humidity of 60% RH, and a notch was subsequently made on each test piece. The thus notched test pieces were left to stand for 5 days in an incubator at a temperature of 23° C. and a humidity of 60% RH, after which the test pieces were taken out of the incubator, and the Charpy impact strength (kJ/m²) was measured in accordance with ISO179-1.

Examples 7-1 to 7-4 and Comparative Examples 7-1 to 7-3

To 2 kg of a homopolypropylene (MFR at 230° C. under a load of 2.16 kg=3 g/10 min), 0.05% by mass of a phenolic antioxidant (tetrakis[methylene-3-(3',5'-di-tert-butyl-4-hydroxyphenyl)propionate]methane), 0.1% by mass of a phosphorus-based antioxidant (tris(2,4-di-text-butylphenyl) phosphite), 0.05% by mass of calcium stearate, and each nucleating agent for polyolefin resin shown in Table 9 in the amount shown in Table 9 were added and manually blended for 3 minutes, and the resultants were each subsequently loaded to a biaxial extruder (TEX-25αIII, manufactured by The Japan Steel Works, Ltd.) and granulated at a melt temperature of 230° C. In Table 9, the "steric structure" of each nucleating agent for polyolefin resin represents the steric structure of an aspartic acid residue, and Z represents one of the above-described groups. In Comparative Example 7-1, granulation was performed in the same procedures as in Example 7-1, except that no nucleating agent for polyolefin resin was added. The thus granulated pellets were dried at 80° C. for 8 hours, after which the pellets were each loaded to a uniaxial extruder equipped with a T-die and a roll, and molded into a 100 μm-thick film at a cylinder temperature of 200° C. and a roll temperature of 120° C. The thus obtained films were each heat-stretched in the MD direction at a stretching ratio of 5 at a heating temperature of 100° C. and a stretching rate of 1,000 mm/min. The resulting films were each further heat-stretched in the TD direction at a stretching ratio of 2 under the same conditions, whereby stretched films were obtained. Thereafter, the stretchability of each film and the void characteristics of each stretched film were evaluated by the below-described procedures. The results thereof are shown in Table 9.

<Stretchability>

The surface of each stretched film obtained in the above-described manner was visually observed, and the stretchability was evaluated based on the following evaluation criteria.

○: The whole film was uniformly stretched.

x: The whole film was not uniformly stretched and had irregularities in the stretched state.

<Void Characteristic>

The surface of each stretched film obtained in the above-described manner was observed under a scanning electron microscope at a magnification of ×5,000, and the void characteristic was evaluated based on the following evaluation criteria.

○: Fine voids were observed throughout the film.

Δ: Fine voids were observed in some parts of the film.

x: No void was observed.

TABLE 9

| | Nucleating agent for polyolefin resin | | | | | Added amount | | Void |
| | Z | M | x | a | b | Steric structure | (% by mass) | Stretchability | characteristic |
|---|---|---|---|---|---|---|---|---|---|
| Example 7-1 | Ph | Na | 1 | 2 | 1 | L | 0.05 | ○ | ○ |
| Example 7-2 | pTolyl | Na | 1 | 2 | 1 | racemic body | 0.05 | ○ | ○ |
| Example 7-3 | Mes | Al(OH) | 2 | 1 | 1 | racemic body | 0.05 | ○ | ○ |
| Example 7-4 | CyH | Na | 1 | 2 | 1 | L | 0.05 | ○ | ○ |
| Comparative Example 7-1 | — | — | — | — | — | — | 0 | x | x |
| Comparative Example 7-2 | N,N'-dicyclohexyl-p-phenylene dicarboximide | | | | | | 0.1 | x | Δ |
| Comparative Example 7-3 | N,N'-dicyclohexyl-2,6-naphthalene dicarboxamide | | | | | | 0.1 | x | Δ |

From the above, the nucleating agent for polyolefin resin according to the present invention was confirmed to have an excellent β crystal-forming effect.

The invention claimed is:

1. A nucleating agent for a polyolefin resin, comprising a compound represented by the following Formula (1):

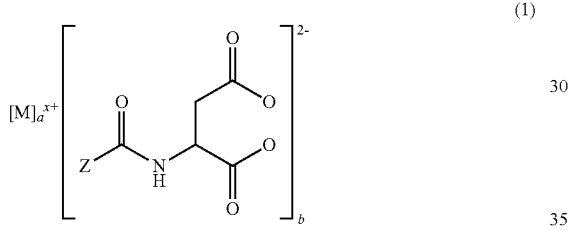

wherein M represents a monovalent to trivalent metal atom having a specific gravity of 4.0 or less, or a hydroxy group-bound divalent or trivalent metal atom having a specific gravity of 4.0 or less, wherein M is not calcium; a represents 1 or 2; b represents 1 or 3; x represents an integer of 1 to 3; ax=2b is satisfied; and Z represents a group represented by the following Formula (2) or (3):

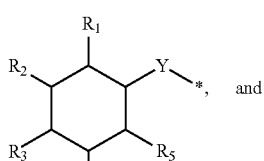

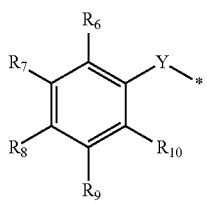

wherein * represents a position at which each group is linked with Z of Formula (1); Y represents a direct bond or an alkylene group having 1 to 4 carbon atoms; and $R_1$ to $R_{10}$ each independently represent a hydrogen atom, a hydroxy group, a halogen atom, an alkyl group having 1 to 10 carbon atoms, a halogenated alkyl group having 1 to 10 carbon atoms, an alkoxy group having 1 to 10 carbon atoms, or an alkenyl group having 2 to 10 carbon atoms.

2. The nucleating agent for a polyolefin resin according to claim 1, wherein M is lithium, sodium, potassium, magnesium, barium, aluminum, hydroxyaluminum, or dihydroxyaluminum.

3. A nucleating agent composition for a polyolefin resin, comprising:
the nucleating agent for a polyolefin resin according to claim 1; and
at least one additive selected from the group consisting of a phenolic antioxidant, a phosphorus-based antioxidant, a sulfur-based antioxidant, other antioxidant, a hindered amine compound, an ultraviolet absorber, a nucleating agent different from the compound represented by Formula (1), a flame retardant, a flame retardant aid, a lubricant, a filler, a hydrotalcite, a fatty acid metal salt, an antistatic agent, a fluorescent brightener, a pigment, and a dye.

4. A polyolefin resin masterbatch, comprising:
a polyolefin resin; and
the nucleating agent for a polyolefin resin according to claim 1.

5. A polyolefin resin composition, comprising:
a polyolefin resin; and
the nucleating agent for a polyolefin resin according to claim 1,
wherein a content of the nucleating agent for a polyolefin resin is 0.001 to 10 parts by mass with respect to 100 parts by mass of the polyolefin resin.

6. The polyolefin resin composition according to claim 5, wherein the polyolefin resin is a polypropylene resin.

7. The polyolefin resin composition according to claim 5, wherein the polyolefin resin comprises an ethylene-propylene copolymer.

8. The polyolefin resin composition according to claim 5, further comprising an elastomer.

9. The polyolefin resin composition according to claim 5, further comprising a filler.

10. A molded article comprising the polyolefin resin composition according to claim 5.

11. The molded article according to claim 10, wherein the molded article is an automotive exterior component.

12. The molded article according to claim 10, wherein the molded article is automotive interior component.

13. The molded article according to claim 10, wherein the molded article is a housing.

14. The molded article according to claim 10, wherein the molded article is a container.

15. The molded article according to claim 10, wherein the molded article is a pipe.

16. A film comprising the polyolefin resin composition according to claim 5.

17. The film according to claim 16, wherein the film is a porous film comprising voids.

18. The film according to claim 17, wherein the film is a light reflection film.

19. The film according to claim 17, wherein the film is a battery separator.

20. A method of producing a porous film, the method comprising:
   a molding step of molding a polyolefin resin composition to obtain a film; and
   a step of heat-stretching the film obtained by the molding step,
   wherein the polyolefin resin composition is the polyolefin resin composition according to claim 5.

21. A package comprising the film according to claim 16.

* * * * *